(12) United States Patent
Zhang et al.

(10) Patent No.: US 11,814,352 B2
(45) Date of Patent: Nov. 14, 2023

(54) SALTS FORMED BY 2-(1-ACYLOXY-N-PENTYL) BENZOIC ACID AND BASIC AMINO ACID OR AMINOGUANIDINE, AND PREPARATION METHOD AND APPLICATION THEREOF

(71) Applicant: JIANGSU KANION PHARMACEUTICAL CO., LTD., Lianyungang (CN)

(72) Inventors: Yihua Zhang, Nanjing (CN); Wei Xiao, Lianyungang (CN); Zhangjian Huang, Nanjing (CN); Jianbing Wu, Nanjing (CN); Jiayi Zhu, Nanjing (CN); Zhenzhong Wang, Lianyungang (CN); Tuanjie Wang, Lianyungang (CN)

(73) Assignee: JIANGSU KANION PHARMACEUTICAL CO., LTD., Lianyungang (CN)

( * ) Notice: Subject to any disclaimer, the term of this patent is extended or adjusted under 35 U.S.C. 154(b) by 431 days.

(21) Appl. No.: 17/276,172

(22) PCT Filed: Dec. 3, 2018

(86) PCT No.: PCT/CN2018/118879
§ 371 (c)(1),
(2) Date: Mar. 15, 2021

(87) PCT Pub. No.: WO2020/107500
PCT Pub. Date: Jun. 4, 2020

(65) Prior Publication Data
US 2022/0024848 A1  Jan. 27, 2022

(30) Foreign Application Priority Data

Nov. 28, 2018 (CN) .......................... 201811440339.8

(51) Int. Cl.
*C07C 69/78* (2006.01)
*A61P 9/10* (2006.01)
(Continued)

(52) U.S. Cl.
CPC ............ *C07C 69/78* (2013.01); *A61K 9/0019* (2013.01); *A61P 9/10* (2018.01); *C07C 227/26* (2013.01);
(Continued)

(58) Field of Classification Search
CPC ....... A61K 9/0019; A61K 31/192; A61P 7/02; A61P 9/10; B09B 2101/85; B09B 3/45;
(Continued)

(56) References Cited

PUBLICATIONS

Zhang et al. (One-Pot Synthesis of 2-(1-acyloxypentyl) benzoic acids, Chinese Chemical Letters, 19, pp. 915-917, Published 2008 (Year: 2008).*

(Continued)

*Primary Examiner* — Yevgeny Valenrod
*Assistant Examiner* — Blaine G Doletski
(74) *Attorney, Agent, or Firm* — CBM PATENT CONSULTING, LLC

(57) ABSTRACT

The present disclosure discloses salts formed by 2-(1-acyloxy-n-pentyl)benzoic acid and basic amino acid or aminoguanidine, a preparation method thereof, pharmaceutical preparations containing these salts, and application thereof in preparation of drugs for preventing or treating ischemic cardiovascular and cerebrovascular diseases, resisting thrombosis and improving cardio-cerebral circulation disorders. The compound of the present disclosure has excellent water solubility, aqueous solution stability and pharmacokinetic properties, also has significant anti-platelet aggregation, anti-thrombosis, anti-cerebral ischemia and neuroprotective activity. The compound of the present disclosure has significantly better effects than those of (S)-butylphthalide (Continued)

and potassium (R/S)-2-(1-hydroxy-n-pentyl) benzoate (PHPB), has significantly lower acute toxicity to mice by intravenous injection than that of butylphthalide and PHPB, has a lower inhibition rate of the hERG potassium channel in CHO-hERG cells than that of (S)-butylphthalide, and has a negative result in Bacterial Reverse Mutation Test (Ames test).

10 Claims, 6 Drawing Sheets

(51) Int. Cl.
  *A61K 9/00* (2006.01)
  *C07C 227/26* (2006.01)
  *C07C 279/14* (2006.01)
  *C07C 281/16* (2006.01)
  *C07D 233/64* (2006.01)
(52) U.S. Cl.
  CPC .......... *C07C 279/14* (2013.01); *C07C 281/16* (2013.01); *C07D 233/64* (2013.01)
(58) Field of Classification Search
  CPC ..... B09B 5/00; C07B 2200/07; C07C 227/26; C07C 229/26; C07C 279/14; C07C 281/16; C07C 69/157; C07C 69/24; C07C 69/78; C07C 277/08; C07C 279/02; C07C 279/12; C07C 67/08; C07D 233/64; C10B 49/02; C10B 53/02; C10L 2200/0469; C10L 2290/148; C10L 2290/58; C10L 2290/60; C10L 5/44; C10L 9/08; D21B 1/36; D21C 1/02; G05D 21/02; G06Q 10/02; G06Q 10/06312; G06Q 10/06314; G06Q 10/06315; G06Q 10/1093; G06Q 50/205; G16C 20/10; G16C 60/00; Y02E 50/10; Y02E 50/30
  See application file for complete search history.

(56) References Cited

PUBLICATIONS

Gupta et al. (Salts of therapeutic Agents: Chemical, Physicochemical, and Biological Considerations, Molecules, 23, pp. 1-15, Published 2018) (Year: 2018).*

* cited by examiner

SALTS FORMED BY 2-(1-ACYLOXY-N-PENTYL) BENZOIC ACID AND BASIC AMINO ACID OR AMINOGUANIDINE, AND PREPARATION METHOD AND APPLICATION THEREOF

TECHNICAL FIELD

The present disclosure belongs to the fields of pharmaceutical chemistry and pharmacotherapeutics, and specifically relates to salts formed by 2-(1-acyloxy-n-pentyl)benzoic acid and basic amino acid or aminoguanidine, a preparation method thereof, pharmaceutical compositions containing the salt compounds, and medical application thereof, especially the application in preparation of drugs for preventing or treating ischemic cardiovascular and cerebrovascular diseases, resisting thrombosis and improving cardio-cerebral circulation disorders.

BACKGROUND ART

3-N-butylphthalide (NBP), abbreviated as butylphthalide, and having a chemical name racemic (R/S)-3-N-butyl-1 (3H)-isobenzofuranone, is a self-developed and marketed drug for treating mild and moderate ischemic stroke in China. Although NBP has certain biological activity in anti-platelet aggregation, anti-thrombosis, reduction of cerebral infarct volume, protection of mitochondrial function, and improvement of cerebral microcirculation, the overall efficacy of a single drug is not high, and NBP is often combined with other drugs in clinical practice. In addition, NBP is an oily substance with a high boiling point, requires high-temperature and high-vacuum distillation for many times to produce a qualified pharmaceutical product, and is difficult to mass-produce. Due to the extremely poor water solubility of NBP, an injection must be encapsulated with hydroxypropyl-β-cyclodextrin and then prepared with sodium chloride and water for injection. Therefore, the production process is relatively complicated and the cost is higher compared with commonly used injections. In order to improve the activity and/or increase the water solubility of NBP, people have modified and transformed the structure of NBP.

Chinese patents ZL 98125618.x and ZL 9910 9673.8 disclose the preparation process of (R)- and (S)—NBP and the anti-platelet aggregation and anti-thrombotic activities thereof, wherein the activity of (S)—NBP is better than that of (R)—NBP and NBP.

Chinese patent ZL 01109795.7 discloses a salt formation method of an NBP ring-opening compound, namely (R/S)-2-(1-hydroxy-n-pentyl)benzoic acid with potassium, sodium, calcium, magnesium, zinc, aniline, benzylamine, morpholine or diethylamine, and application thereof, wherein the potassium salt ((R/S)—PHPB, PHPB for short) has high water solubility, can be converted into NBP in the body to exert the anti-cerebral ischemia activity, and has bioavailability better than NBP (*Acta Pharmacol. Sin.*, 2018, 39, 275-285).

Chinese patent ZL 200410048268.9 discloses a process and activity of salts formed by (S)-2-(1-hydroxy-n-pentyl) benzoic acid with monovalent metal ions lithium, sodium and potassium, or divalent metal ions magnesium, calcium and zinc, or organic bases benzylamine, tert-butylamine, N,N'-dibenzylethylenediamine, wherein potassium (S)-2-(1-hydroxy-n-pentyl) benzoate ((S)—PHPB) has better anti-cerebral ischemia activity than (R)—PHPB and (S)—NBP.

Chinese patent ZL 201110115922.3 discloses a preparation method and medical application of thio and seleno homologs of NBP, wherein the thio homologs have better anti-cerebral ischemia and antioxidant activity than NBP.

Currently PHPB and (S)—NBP have entered phase II-III and phase I-II clinical studies respectively, for the treatment of ischemic stroke.

The applicant previously designed and synthesized L-arginine (R/S)-2-(1-hydroxy-n-pentyl) benzoate (AHPB) (Gao Yang, Master's thesis of China Pharmaceutical University, 2016). Studies have shown that AHPB has excellent water solubility, and better anti-platelet aggregation, anti-cerebral ischemia and nerve protection activity than equimolar NBP, but has poor chemical stability.

SUMMARY OF THE DISCLOSURE

Objective of the disclosure: In view of the prior art, the disclosure provides a compound I obtained by reacting 2-(1-acyloxy-n-pentyl)benzoic acid with basic amino acid or aminoguanidine, and provides a preparation method of the new compound I, a pharmaceutical composition containing these compounds, and pharmaceutical application thereof.

Technical solution: A compound of General Formula I is described in the present application,

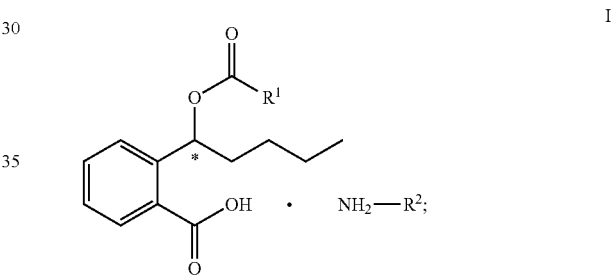

I wherein:

R$^1$ is C$_1$-C$_8$ alkyl, aryl or heteroaryl; and

H$_2$N—R$^2$ is basic amino acid or aminoguanidine, wherein the chiral center of the 2-(1-acyloxy-n-pentyl) benzoic acid moiety represented by * is of an (R)-, (S)- or (R/S)-configuration.

Preferably, R$^1$ is methyl, ethyl, n-propyl or phenyl.

Preferably, the basic amino acid is L-arginine, L-lysine or L-histidine.

Further preferably, the compound of General Formula I is selected from the following compounds:

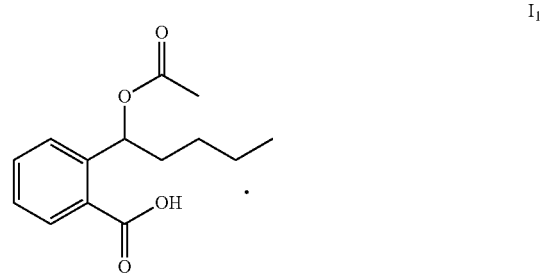

I$_1$

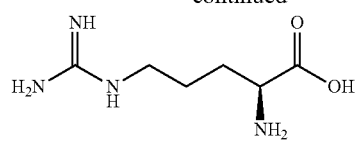

L-arginine (R/S)-2-(1-acetoxy-n-pentyl) benzoate;

I₂

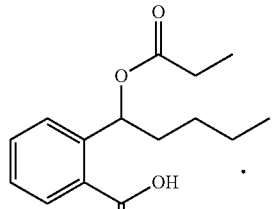

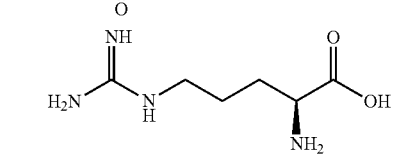

L-arginine (R/S)-2-(1-propionyloxy-n-pentyl) benzoate;

I₃

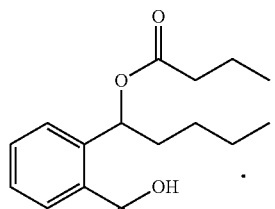

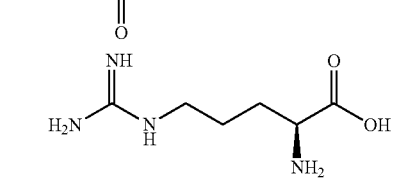

L-arginine (R/S)-2-(1-N-butyryloxy-n-pentyl) benzoate;

I₄

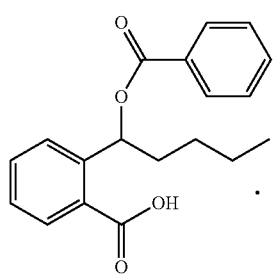

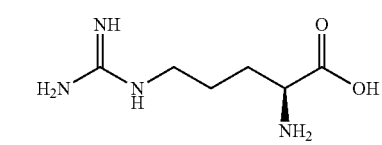

L-arginine (R/S)-2-(1-benzyloxy-n-pentyl) benzoate;

I₅

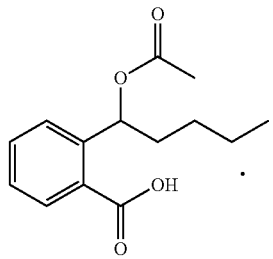

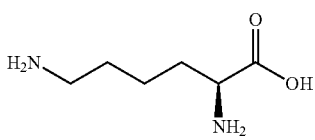

L-lysine (R/S)-2-(1-acetoxy-n-pentyl) benzoate;

I₆

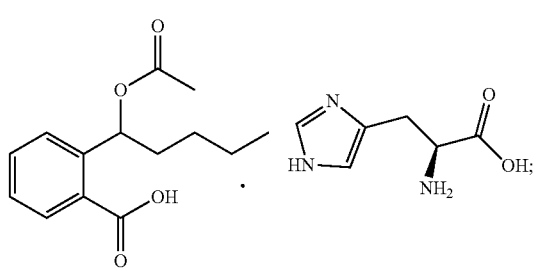

L-hisitidine (R/S)-2-(1-acetoxy-n-pentyl) benzoate

I₇

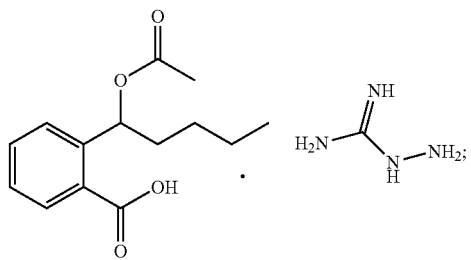

aminoguanidine (R/S)-2-(1-acetoxy-n-pentyl) benzoate

I₁ᵣ

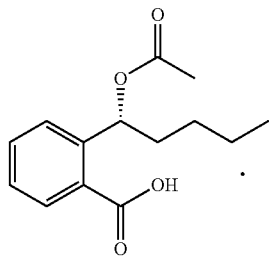

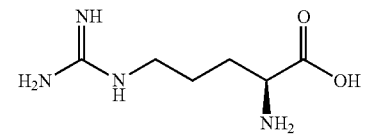

L-arginine (R)-2-(1-acetoxy-n-pentyl) benzoate;

-continued

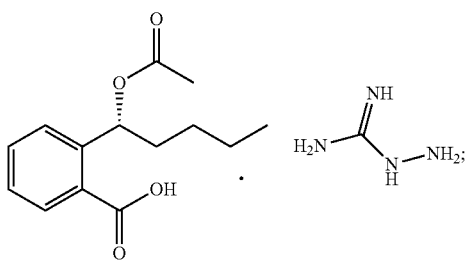

aminoguanidine (R)-2-(1-acetoxy-n-pentyl) benzoate

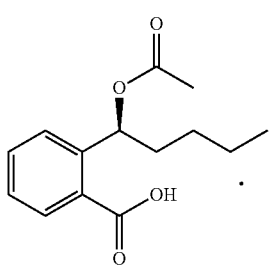

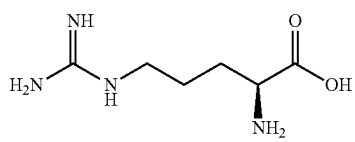

L-arginine (S)-2-(1-acetoxy-n-pentyl) benzoate;

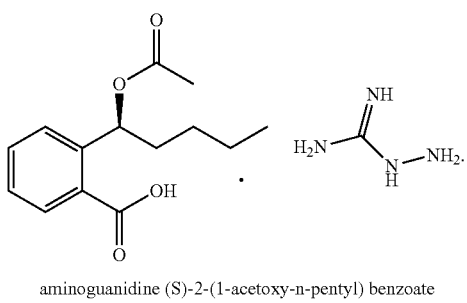

aminoguanidine (S)-2-(1-acetoxy-n-pentyl) benzoate

The disclosure further discloses a preparation method of the compound of General Formula I, including the following steps:

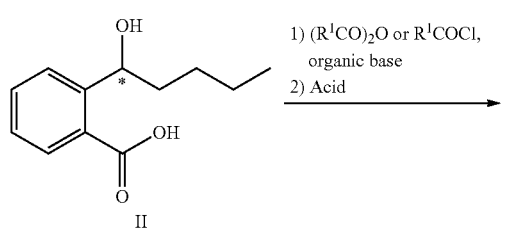

-continued

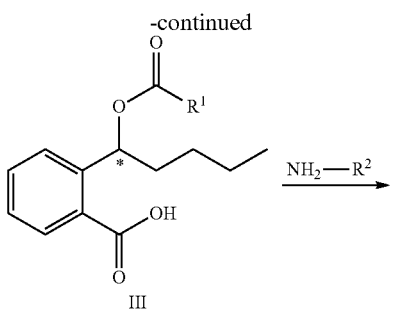

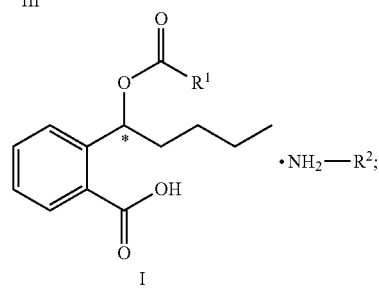

(1) at low temperature and in the presence of an organic base, adding acid anhydride or acyl chloride dropwise to an organic solvent solution of a compound II, and acidifying the reaction solution after the reaction for precipitating a white solid compound III; and (2) dissolving the compound III obtained in step (1) in alcohol, adding $H_2N-R^2$ to form a salt, and after the reaction, filtering and recrystallizing the precipitate with alcohol to obtain a compound I.

Further, in step (1), the reaction temperature is −30 to −5° C.; the organic base is 4-dimethylaminopyridine, diethylamine, triethylamine or pyridine; the organic solvent is one or a combination of two of diethyl ether, tetrahydrofuran, dichloromethane, trichloromethane or acetone; the acid is concentrated or dilute hydrochloric acid, sulfuric acid or nitric acid; and the reaction solution is acidified to pH 2-6.

In step (2), the reaction temperature is −5 to 30° C., the alcohol is ethanol, methanol, propanol or isopropanol, and the basic amino acid is L-arginine, L-lysine or L-histidine.

The disclosure discloses a pharmaceutical composition, including the compound I and a pharmaceutically acceptable carrier.

The application of the compound I in preparation of drugs for preventing or treating ischemic cardiovascular and cerebrovascular diseases, resisting thrombosis and improving cardio-cerebral circulation disorders is also within the protection scope of the disclosure.

Various dosage forms of the pharmaceutical composition of the disclosure can be prepared by those skilled in the art according to conventional production methods in the pharmaceutical field. For example, the active ingredient is mixed with one or more carriers (also called excipients), and then prepared into the desired dosage form, including tablets, capsules, and granules. The active ingredient can also be made into intravenous injection or lyophilized intravenous injection according to the conventional production method of injection.

The compound and the pharmaceutical composition of the disclosure can be used to prepare drugs for preventing and treating ischemic cardiovascular and cerebrovascular diseases, resisting thrombosis and improving cardio-cerebral circulation disorders, such as myocardial infarction, angina pectoris, arrhythmia, coronary heart disease, cerebral infarction and stroke.

Beneficial effects: The compound of the disclosure has the following excellent properties: (1) excellent water solubility and aqueous solution stability, which is convenient for the pharmaceutical industry to process an intravenous injection or lyophilized intravenous injection suitable for medication for patients with ischemic stroke; (2) release of two types of active fragments that can act synergistically in the body, and significant enhancement of anti-ischemic stroke treatment effect by (R/S)-, (R)- or (S)—NBP and certain basic amino acid or aminoguanidine acting synergistically in the body; (3) significant anti-cerebral ischemia and neuroprotective activity; (4) excellent pharmacokinetic properties; and (5) higher safety. The details are as follows:

The compound I of the disclosure is a solid compound with good water solubility and aqueous solution stability, and can release the corresponding 2-(1-acyloxy-n-pentyl) benzoic acid and basic amino acid or aminoguanidine in the body. The 2-(1-acyloxy-n-pentyl)benzoic acid can be further hydrolyzed by esterase to remove the acyl group, generating (R/S)-, (R)- and (S)-2-(1-hydroxy-n-pentyl)benzoic acid respectively, which are cyclized to corresponding (R/S)-, (R)- and (S)—NBP, respectively, to exert an anti-cerebral ischemia effect; and the basic amino acid or aminoguanidine also has extremely important normal and pharmacological effects. L-arginine can be metabolized by nitric oxide (NO) synthase (NOS) in the body into NO beneficial to the cardiovascular system (Proc. Nutr. Soc., 2018, 77, 112-123). Dietary supplementation of L-arginine can reduce platelet reactivity in patients with high cholesterol (J Am Coll Cardiol, 1997, 29, 479-485) and prevent atherosclerosis (J Clin Invest, 1992, 90, 1168-1172). L-arginine can enter the brain from peripheral blood through the cationic amino acid transporter (CAT1) on the blood-brain barrier (BBB), which is very important for brain development (Microvasc. Res., 2018, 117, 16-21). In addition, intravenous drip or oral administration of L-arginine in patients with MELAS type mitochondrial encephalopathy can increase cerebral blood flow microcirculation, reduce acute focal cerebral ischemia injury, and significantly reduce the frequency and severity of stroke symptoms (Neurology, 2005, 64, 710-712). Direct injection of L-arginine into the cerebral ventricle of AD rats can produce significant neuroprotective and anti-apoptotic activity (Transl. Neurosci., 2018, 9, 43-53). L-lysine and L-histidine are essential amino acids for the human body, and play an important role in nerve signal transmission and energy supply Aminoguanidine has anti-cerebral ischemia (Neurosciences, 2012, 17, 121-126), neuroprotection (Neurochem. Int., 2010, 56, 634-641) and anti-aging (J. Proteomics, 2017, 156, 104-112) activity. Therefore, (R/S)-, (R)- or (S)—NBP acts synergistically with one of the above basic amino acid or aminoguanidine in the body to enhance the therapeutic effect. The results of in vivo and in vitro studies indicate that the compound of the disclosure has significant anti-platelet aggregation, anti-thrombosis, anti-cerebral ischemia and neuroprotective activity, wherein the salt formed by the acid of the (S)-isomer is better than the salt formed by the acid of the (R)-isomer or the acid of the (R/S)-racemate, and is significantly better than (S)—NBP and PHPB. The compounds of the disclosure also have excellent pharmacokinetic properties. In addition, the compounds of the disclosure have significantly lower acute toxicity to mice by intravenous injection than that of NBP and PHPB, a lower inhibition rate of hERG potassium channel in CHO-hERG cells than that of (S)—NBP, and a negative result of Bacterial Reverse Mutation Test (Ames test).

DETAILED DESCRIPTION OF THE INVENTION

Figure 1:
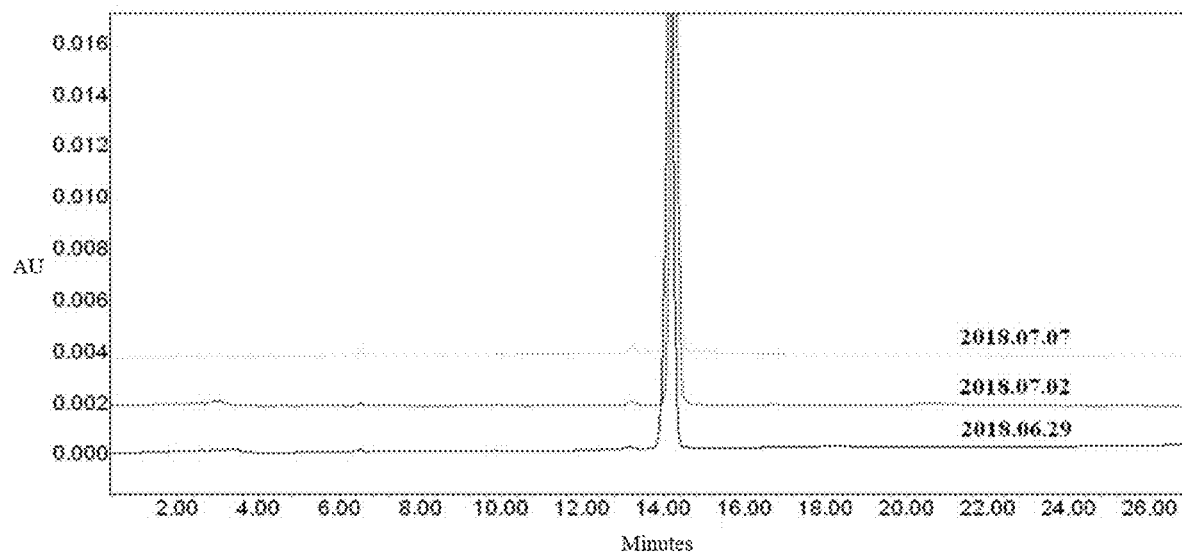
FIG. 1 is a sample solution stability analysis spectrogram of compound $I_{1s}$ in $H_2O$.

The present application will be described in detail below in conjunction with specific examples.

Material Source:

(S)-butylphthalide ((S)—NBP) is prepared by referring to the method of Chinese patent ZL 98125618.x.

Potassium (R/S)-2-(1-hydroxy-n-pentyl) benzoate (PHPB) is prepared by referring to the method of Chinese patent ZL 01109795.7.

(R/S)-, (R)- and (S)-2-(1-hydroxy-n-pentyl)benzoic acids are prepared by referring to the method of Chinese patent ZL 200410048268.9.

Aspirin, L-arginine, and Edaravone were purchased from Saen Chemical Technology Co., Ltd.

Clopidogrel was purchased from Shanghai Yuanye Bio-Technology Co., Ltd.

Example 1: Preparation of L-Arginine (R/S)-2-(1-Acetoxy-n-Pentyl) Benzoate ($I_1$)

Under the condition of −30 to −5° C., 21.8 mL of (157.8 mmol) triethylamine and 0.6 g of (5.2 mol) DMAP were added to a solution of 10.9 g of (52.6 mmol) (R/S)-2-(1-hydroxy-n-pentyl)benzoic acid (II) in diethyl ether (300 mL), then 11.1 mL of (157.8 mmol) acetyl chloride was added dropwise slowly, and the mixed solution was stirred for 5 hours. After the reaction, about 35 mL of 10% hydrochloric acid was added for acidifying the reaction solution to pH 2-3. The reaction solution was stirred for 2 hours. The organic layer was separated, dried with anhydrous $Na_2SO_4$, filtered, concentrated under reduced pressure, and subjected to column chromatography [petroleum ether:ethyl acetate (v:v)=10:1] to obtain 9.96 g of white needle-like crystals (R/S)-2-(1-acetoxy-n-pentyl)benzoic acid with a yield of 76%; m.p.: 65-66° C.; MS (m/z): 249 $[M_1-H]^-$; $^1H$ NMR (300 MHz, $CDCl_3$): δ (ppm): 0.97 (t, 3H, $CH_3$, J=6.9 Hz), 1.38-1.52 (m, 4H, $CH_2CH_2CH_3$), 1.84-1.99 (m, 2H, $CHCH_2CH_2$), 2.17 (s, 3H, $CHOCOCH_3$), 6.69 (dd, 1H, $CH_2CHOCOCH_3$, $J_1$=8.1 Hz, $J_2$=4.5 Hz), 7.38-7.44 (m, 1H, ArH), 7.56-7.65 (m, 2H, ArH), 8.09-8.12 (m, 1H, ArH); $^{13}C$ NMR (75 MHz, $CDCl_3$): δ (ppm): 174.4, 131.2, 128.8, 128.3, 127.2, 74.9, 61.1, 54.4, 40.5, 27.6, 27.2, 23.9, 21.7, 13.3.

Under the condition of −5 to 30° C., 9.96 g of (39.8 mmol) (R/S)-2-(1-acetoxy-n-pentyl)benzoic acid was dissolved in 25 mL of absolute ethanol. Under stirring, 6.9 g of (39.8 mmol) L-arginine was added to form a salt. The precipitate was filtered and recrystallized with 95% ethanol to obtain 9.4 g of white powdery solid $I_1$ with a yield of 56%; m.p.: 178-179° C.; $[α]^{20}_D$=+5.2° (c=1.00, $CH_3OH$); MS (m/z): 249 $[M_1-H]^-$, 175 $[M_2+H]^+$; $^1H$ NMR (300 MHz, $D_2O$): δ (ppm): 0.80 (t, 3H, $CH_3$, J=6.0 Hz), 1.10-1.30 (m, 4H, $CH_2CH_2CH_3$), 1.54-1.72 (m, 2H, $CHCH_2CH_2$), 1.81-1.88 (m, 4H, $CH_2CH_2CHCOOH$), 2.06 (s, 3H, $CHOCOCH_3$), 3.18 (t, 2H, $NHCH_2CH_2$, J=6.9 Hz), 3.70 (dd, 1H, $CH_2CHCOOH$, $J_1$=7.5 Hz, $J_2$=6.0 Hz), 6.10 (dd, 1H, $CH_2CHOCOCH_3$, $J_1$=8.1 Hz, $J_2$=6.6 Hz), 7.29-7.43 (m, 4H, ArH); $^{13}C$ NMR (75 MHz, $D_2O$): δ (ppm): 177.5, 174.3, 173.8, 138.1, 136.8, 128.7, 127.7, 126.9, 125.8, 74.9, 54.4, 40.6, 35.2, 27.6, 27.2, 24.5, 23.9, 21.7, 20.7, 13.3.

Example 2: Preparation of L-Arginine (R/S)-2-(1-Propionyloxy-n-Pentyl) Benzoate ($I_2$)

Under the condition of −30 to −5° C., 21.8 mL of (157.8 mmol) triethylamine and 0.6 g of (5.2 mol) DMAP were added to a solution of 9.96 g of (39.8 mmol) (R/S)-2-(1-hydroxy-n-pentyl)benzoic acid (II) in diethyl ether (300 mL), then 13.1 mL of (157.8 mmol) propionyl chloride was added dropwise slowly, and the mixed solution was stirred for 5 hours. After the reaction, about 35 mL of 10% hydrochloric acid was added for acidifying the reaction solution to pH 2-3. The reaction solution was stirred for 2 hours. The organic layer was separated, dried with anhydrous $Na_2SO_4$, filtered, concentrated under reduced pressure, and subjected to column chromatography [petroleum ether:ethyl acetate (v:v)=10:1] to obtain 9.0 g of oily (R/S)-2-(1-propionyloxy-n-pentyl)benzoic acid with a yield of 65%; MS (m/z): 263 $[M_1-H]^-$; $^1H$ NMR (300 MHz, $CDCl_3$): δ (ppm): 0.96 (t, 3H, $CH_2CH_2CH_3$, J=6.9 Hz), 1.21 (t, 3H, $COCH_2CH_3$, J=7.8 Hz), 1.32-1.51 (m, 4H, $CH_2CH_2CH_3$), 1.80-1.98 (m, 2H, $CHCH_2CH_2$), 2.43 (q, 2H, $COCH_2CH_3$, J=7.5 Hz), 6.68 (dd, 1H, $CH_2CHOCOCH_2$, $J_1$=8.1 Hz, $J_2$=6.6 Hz), 7.33-7.44 (m, 1H, ArH), 7.52-7.64 (m, 2H, ArH), 8.03-8.10 (m, 1H, ArH); $^{13}C$ NMR (75 MHz, $CDCl_3$): δ (ppm): 172.8, 171.3, 143.8, 133.5, 130.6, 126.7, 125.7, 72.3, 36.0, 25.9, 27.4, 21.7, 17.9, 13.4, 13.1.

Under the condition of −5 to 30° C., the oily product was dissolved in 25 mL of absolute ethanol. Under stirring, 5.9 g of (33.9 mol) L-arginine was added to form a salt. The precipitate was filtered and recrystallized with 95% ethanol to obtain 7.8 g of white powdery solid $I_2$ with a yield of 52%; m.p.: 169-171° C.; $[α]^{20}_D$=+5.5° (c=1.00, $CH_3OH$); MS (m/z): 263 $[M_1-H]^-$, 175 $[M_2+H]^+$; $^1H$ NMR (300 MHz, $D_2O$): δ (ppm): 0.81 (t, 3H, $CH_2CH_2CH_3$, J=6.0 Hz), 1.06 (t, 3H, $COCH_2CH_3$, J=7.5 Hz), 1.18-1.37 (m, 4H, $CH_2CH_2CH_3$), 1.53-1.73 (m, 2H, $CHCH_2CH_2$), 1.83-1.91 (m, 4H, $CH_2CH_2CHCOOH$), 2.38 (q, 2H, $COCH_2CH_3$, J=7.5 Hz), 3.19 (t, 2H, $NHCH_2CH_2$, J=6.9 Hz), 3.72 (dd, 1H, $CH_2CHCOOH$, $J_1$=7.5 Hz, $J_2$=6.0 Hz), 6.18 (dd, 1H, $CH_2CHOCOCH_2$, $J_1$=8.1 Hz, $J_2$=6.6 Hz), 7.30-7.43 (m, 4H, ArH); $^{13}C$ NMR (75 MHz, $D_2O$): δ (ppm): 179.9, 179.8, 176.9, 159.4, 140.9, 139.1, 131.5, 130.2, 129.6, 128.2, 77.2, 56.9, 43.1, 38.0, 30.3, 20.1, 29.9, 26.5, 24.3, 15.9, 11.1.

Example 3: Preparation of L-Arginine (R/S)-2-(1-N-Butyryloxy-n-Pentyl) Benzoate ($I_3$)

Under the condition of −30 to −5° C., 21.8 mL of (157.8 mmol) triethylamine and 0.6 g of (5.2 mol) DMAP were added to a solution of 9.96 g of (39.8 mmol) (R/S)-2-(1-hydroxy-n-pentyl)benzoic acid (II) in diethyl ether (300 mL), then 15.9 mL of (157.8 mmol) n-butyryl chloride was added dropwise slowly, and the mixed solution was stirred for 5 hours. After the reaction, about 35 mL of 10% hydrochloric acid was added for acidifying the reaction solution to pH 2-3. The reaction solution was stirred for 2 hours. The organic layer was separated, dried with anhydrous $Na_2SO_4$, filtered, concentrated under reduced pressure, and subjected to column chromatography [petroleum ether:ethyl acetate (v:v)=10:1] to obtain 8.4 g of oily (R/S)-2-(1-N-butyryloxy-n-pentyl)benzoic acid with a yield of 58%; MS (m/z): 277 $[M_1-H]^-$; $^1H$ NMR (300 MHz, $CDCl_3$): δ (ppm): 0.89-1.06 (m, 6H, 2×$CH_3$), 1.33-1.51 (m, 4H, $CH_2CH_2CH_2CH_3$), 1.7-1.78 (m, 2H, $COCH_2CH_2CH_3$), 1.85-1.98 (m, 2H, $CHCH_2CH_2$), 2.41 (t, 2H, $COCH_2CH_2$, J=7.5 Hz), 6.70 (dd, 1H, $CH_2CHOCOCH_2$, $J_1$=8.1 Hz, $J_2$=4.5 Hz), 7.35-7.45 (m, 1H, ArH), 7.55-7.64 (m, 2H, ArH), 8.06-8.11 (m, 1H, ArH); $^{13}C$ NMR (75 MHz, $CDCl_3$): δ (ppm): 173.6, 171.4, 143.9, 132.5, 130.1, 128.1, 126.9, 125.5, 72.4, 36.1, 33.9, 21.5, 21.3, 21.7, 13.4, 8.5.

Under the condition of −5 to 30° C., the oily product was dissolved in 25 mL of absolute ethanol. Under stirring, 5.2 g of (29.9 mol) L-arginine was added to form a salt. The precipitate was filtered and recrystallized with 95% ethanol to obtain 7.3 g of white powdery solid $I_3$ with a yield of 54%; m.p.:152-153° C.; $[α]^{20}_D$=+4.6° (c=1.00, $CH_3OH$); MS (m/z): 277 $[M_1-H]^-$, 175 $[M_2+H]^+$; $^1H$ NMR (300 MHz, $D_2O$): δ (ppm): 0.71-0.84 (m, 6H, 2×$CH_3$), 1.18-1.36 (m, 4H, $CH_2CH_2CH_2CH_3$), 1.5-1.58 (m, 2H, $COCH_2CH_2CH_3$), 1.63-1.73 (m, 2H, $CHCH_2CH_2$), 1.73-1.95 (m, 4H, $CH_2CH_2CHCOOH$), 2.26 (t, 2H, $CHOCOCH_2CH_2$, J=7.2 Hz), 3.19 (t, 2H, $NHCH_2CH_2$, J=6.6 Hz), 3.74 (dd, 1H, $CH_2CHCOOH$, $J_1$=7.5 Hz, $J_2$=6.0 Hz), 6.34 (dd, 1H, $CH_2CHOCOCH_2$, $J_1$=8.1 Hz, $J_2$=6.6 Hz), 7.23-7.49 (m, 4H, ArH); $^{13}C$ NMR (75 MHz, $D_2O$): δ (ppm): 176.1, 175.2, 174.3, 156.9, 138.3, 131.5, 129.1, 127.8, 127.4, 125.3, 74.3, 54.4, 40.5, 36.3, 35.8, 27.6, 27.4, 24.1, 21.9, 18.2, 13.4, 13.1.

Example 4: Preparation of L-Arginine (R/S)-2-(1-Benzoyloxy-n-Pentyl) Benzoate ($I_4$)

Under the condition of −30 to −5° C., 21.8 mL of (157.8 mmol) triethylamine and 0.6 g of (5.2 mmol) DMAP were added to a solution of 9.96 g of (39.8 mmol) (R/S)-2-(1-hydroxy-n-pentyl)benzoic acid (II) in diethyl ether (300 mL), then 21.1 mL of (157.8 mmol) benzoyl chloride was added dropwise slowly, and the mixed solution was stirred for 5 hours. After the reaction, about 35 mL of 10% hydrochloric acid was added for acidifying the reaction solution to pH 2-3. The reaction solution was stirred for 2 hours. The organic layer was separated, dried with anhydrous $Na_2SO_4$, filtered, concentrated under reduced pressure, and subjected to column chromatography [petroleum ether:ethyl acetate (v:v)=10:1] to obtain 10.0 g of oily (R/S)-2-(1-benzoyloxy-n-pentyl)benzoic acid with a yield of 61%; MS (m/z): 311[$M_1$–H]$^-$; $^1$H NMR (300 MHz, $CDCl_3$): δ (ppm): 0.99 (t, 3H, $CH_3$, J=7.2 Hz), 1.33-1.63 (m, 4H, $CH_2\underline{CH_2CH_2}CH_3$), 2.03-2.12 (m, 2H, $CHC\underline{H_2}CH_2$), 6.94 (dd, 1H, $CH_2C\underline{H}OCOAr$, $J_1$=7.5 Hz, $J_2$=6.0 Hz), 7.40-7.45 (m, 1H, ArH), 7.45-7.72 (m, 5H, ArH), 8.13-8.22 (m, 3H, ArH); $^{13}$C NMR (75 MHz, $CDCl_3$): δ (ppm): 171.4, 165.8, 143.8, 133.2, 132.1, 132.5, 130.8, 129.7, 129.1, 126.9, 126.8, 125.5, 73.8, 73.3, 36.2, 27.6, 22.0, 21.8, 13.4.

Under the condition of −5 to 30° C., the oily product was dissolved in 25 mL of absolute ethanol. Under stirring, 5.5 g of (31.6 mmol) L-arginine was added to form a salt. The precipitate was filtered and recrystallized with 95% ethanol to obtain 8.8 g of white powdery solid $I_4$ with a yield of 58%; m.p.: 113-115° C.; $[α]^{20}_D$=+3.8° (c=1.00, $CH_3OH$); MS (m/z): 311[$M_1$–H]$^-$, 175 [$M_2$+H]$^+$; $^1$H NMR (300 MHz, $D_2O$): δ (ppm): 0.83 (t, 3H, $CH_3$, J=7.2 Hz), 1.22-1.42 (m, 4H, $C\underline{H_2CH_2}CH_3$), 1.56-1.72 (m, 2H, $CHC\underline{H_2}CH_2$), 1.72-2.07 (m, 4H, $C\underline{H_2}CH_2CHCOOH$), 3.12 (t, 2H, $NHC\underline{H_2}CH_2$), 3.38 (dd, 1H, $CH_2C\underline{H}COOH$, $J_1$=7.5 Hz, $J_2$=6.0 Hz), 7.00 (dd, 1H, $CH_2C\underline{H}OCOAr$, $J_1$=7.5 Hz, $J_2$=6.0 Hz), 7.15-7.24 (m, 1H, ArH), 7.29-7.39 (m, 2H, ArH), 7.43-7.47 (m, 1H, ArH), 7.51-7.56 (m, 1H, ArH), 7.63-7.68 (m, 1H, ArH), 7.72-7.75 (m, 1H, ArH), 7.89-7.91 (m, 1H, ArH), 8.00-8.08 (m, 1H, ArH); $^{13}$C NMR (75 MHz, $D_2O$): δ (ppm): 174.4, 133.8, 131.1, 129.5, 128.9, 128.8, 128.7, 128.3, 127.7, 127.0, 125.7, 114.7, 105.3, 84.1, 80.1, 75.4, 54.4, 40.5, 35.6, 27.6, 27.3, 23.9, 21.7, 15.1, 13.3.

Example 5: Preparation of L-Lysine (R/S)-2-(1-Acetoxy-n-Pentyl) Benzoate ($I_5$)

Under the condition of −5 to 30° C., 9.96 g of (39.8 mmol) (R/S)-2-(1-acetoxy-n-pentyl)benzoic acid (prepared by the method of Example 1) was dissolved in 25 mL of absolute ethanol. Under stirring, 5.7 g of (39.0 mmol) L-lysine was added to form a salt. The precipitate was filtered and recrystallized with 95% ethanol to obtain 7.6 g of light yellow powdery solid $I_5$ with a yield of 49%; m.p.: 122-124° C.; $[α]^{20}_D$=+4.8° (c=1.00, $CH_3OH$); MS (m/z): 249 [$M_1$–H]$^-$, 147 [$M_2$+H]$^+$; $^1$H NMR (300 MHz, $D_2O$): δ ppm: 0.93 (s, 6H, 2×$CH_3$), 1.28-1.48 (m, 4H, $C\underline{H_2CH_2}CH_3$), 1.47-1.67 (m, 2H, $CHC\underline{H_2}CH_2$), 1.71-1.86 (m, 2H, $C\underline{H_2}CHCOOH$), 1.86-2.03 (m, 4H, $NH_2CH_2C\underline{H_2}CH_2$), 2.18 (s, 3H, $CHOCOC\underline{H_3}$), 3.09 (m, 2H, $NH_2C\underline{H_2}CH_2CH_2$), 3.82 (dd, 1H, $CH_2C\underline{H}COOH$, $J_1$=7.5 Hz, $J_2$=6.0 Hz), 6.28 (dd, 1H, $CH_2C\underline{H}OCOCH_3$, $J_1$=8.1 Hz, $J_2$=6.6 Hz), 7.35-7.60 (m, 4H, ArH); $^{13}$C NMR (75 MHz, $D_2O$): δ (ppm): 177.1, 176.3, 141.0, 139.1, 131.5, 130.3, 129.0, 128.4, 77.5, 57.1, 41.1, 37.9, 32.4, 29.8, 29.0, 24.4, 24.1, 23.3, 19.5, 15.9.

Example 6: Preparation of L-Histidine (R/S)-2-(1-Acetoxy-n-Pentyl) Benzoate ($I_6$)

Under the condition of −5 to 30° C., 9.96 g of (39.8 mmol) (R/S)-2-(1-acetoxy-n-pentyl)benzoic acid (prepared by the method of Example 1) was dissolved in 25 mL of absolute ethanol. Under stirring, 6.1 g of (39.3 mmol) L-histidine was added to form a salt. The precipitate was filtered and recrystallized with 95% ethanol to obtain 8.4 g of white powdery solid 16 with a yield of 53%; m.p.: 137-139° C.; $[α]^{20}_D$=+2.4° (c=1.00, $CH_3OH$); MS (m/z): 249 [$M_1$–H]$^-$, 156 [$M_2$+H]$^+$; $^1$H NMR (300 MHz, $D_2O$): δ ppm: 0.88 (s, 6H, 2×$CH_3$), 1.21-1.43 (m, 4H, $C\underline{H_2CH_2}CH_3$), 1.81-2.00 (m, 2H, $CHC\underline{H_2}$), 2.14 (s, 3H, $CHOCOC\underline{H_3}$), 3.25-3.36 (m, 2H, $C\underline{H_2}C\underline{H}COOH$), 4.05 (dd, 1H, $CH_2C\underline{H}COOH$, $J_1$=7.5 Hz, $J_2$=6.0 Hz), 6.19 (dd, 1H, $CH_2C\underline{H}OCOCH_3$, $J_1$=8.1 Hz, $J_2$=6.6 Hz), 7.28-7.35 (m, 1H, ArH), 7.38 (s, 1H, NHC$\underline{H}$=C), 7.41-7.53 (m, 3H, ArH), 8.42 (s, 1H, NHC$\underline{H}$=N); $^{13}$C NMR (75 MHz, $D_2O$): δ (ppm): 177.3, 173.8, 172.8, 138.3, 136.9, 134.7, 128.9, 127.7, 126.9, 125.8, 117.5, 101.2, 74.9, 53.9, 35.2, 27.2, 26.5, 21.7, 20.7, 13.3.

Example 7: Preparation of Aminoguanidine (R/S)-2-(1-Acetoxy-n-Pentyl) Benzoate ($I_7$)

5.3 g of (39.8 mol) aminoguanidine bicarbonate was dissolved in 50 ml of water. Under stirring, the solution was slowly heated to 60° C. After cooling, under the condition of −5 to 30° C., a solution of 9.96 g of (39.8 mmol) (R/S)-2-(1-acetoxy-n-pentyl)benzoic acid (prepared by the method of Example 1) in absolute ethanol (25 mL) was added. The reaction solution was concentrated to dryness under reduced pressure and recrystallized with 95% ethanol to obtain 6.5 g of white powdery solid $I_7$ with a yield of 43%; m.p.: 109-111° C.; MS (m/z): 249 [$M_1$–H]$^-$, 75 [$M_2$+H]$^+$; $^1$H NMR (300 MHz, $D_2O$): δ ppm: 0.97 (t, 3H, $CH_3$, J=6.9 Hz), 1.38-1.52 (m, 4H, $C\underline{H_2CH_2}CH_3$), 1.84-1.99 (m, 2H, $CHC\underline{H_2}CH_2$), 2.17 (s, 3H, $CHOCOC\underline{H_3}$), 6.69 (dd, 1H, $CH_2C\underline{H}OCOCH_3$, $J_1$=8.1 Hz, $J_2$=4.5 Hz), 7.38-7.44 (m, 1H, ArH), 7.56-7.65 (m, 2H, ArH), 8.09-8.12 (m, 1H, ArH); $^{13}$C NMR (75 MHz, $D_2O$): δ (ppm): 174.4, 158.1, 131.2, 128.8, 128.3, 127.2, 74.9, 61.1, 54.4, 40.5, 27.6, 27.2, 23.9, 21.7, 13.3.

Example 8: Preparation of L-Arginine (R)-2-(1-Acetoxy-n-Pentyl) Benzoate ($I_{1r}$)

Under the condition of −30 to −5° C., 5.7 mL of (72.0 mmol) pyridine was added to a solution of (R)-2-(1-hydroxy-n-pentyl)benzoic acid (5.0 g, 24.0 mmol) in dichloromethane (150 mL), then 7.2 mL of (72.0 mmol) acetic anhydride was added dropwise slowly, and the solution was stirred for 5 hours. After the reaction, about 20 mL of 10% hydrochloric acid was added for acidifying the reaction solution to pH 2-3. The reaction solution was stirred for 2 hours. The organic layer was separated, dried with anhydrous $Na_2SO_4$, filtered, concentrated under reduced pressure, and subjected to column chromatography [petroleum ether:ethyl acetate (v:v)=10:1] to obtain 4.8 g of white needle-like crystals (R)-2-(1-acetoxy-n-pentyl)benzoic acid with a yield of 81%; m.p.: 65-66° C.; $[α]^{20}_D$=+38.2° (c=1.00, $CH_3OH$); MS (m/z): 249 [$M_1$–H]$^-$; $^1$H NMR (300 MHz, $CDCl_3$): δ (ppm): 0.97 (t, 3H, $CH_3$, J=6.9 Hz), 1.38-1.52 (m, 4H, $C\underline{H_2CH_2}CH_3$), 1.84-1.99 (m, 2H, $CHC\underline{H_2}CH_2$), 2.17 (s, 3H, $CHOCOC\underline{H_3}$), 6.69 (dd, 1H, $CH_2C\underline{H}OCOCH_3$, $J_1$=8.1 Hz, $J_2$=4.5 Hz), 7.38-7.44 (m, 1H, ArH), 7.56-7.65 (m, 2H, ArH), 8.09-8.12 (m, 1H, ArH); $^{13}$C NMR (75 MHz, $CDCl_3$): δ (ppm): 174.4, 131.2, 128.8, 128.3, 127.2, 74.9, 61.1, 54.4, 40.5, 27.6, 27.2, 23.9, 21.7, 13.3.

Under the condition of −5 to 30° C., 4.8 g of (19.2 mmol) (R)-2-(1-acetoxy-n-pentyl)benzoic acid was dissolved in 25 mL of absolute ethanol. Under stirring, 3.3 g of (19.2 mmol) L-arginine was added to form a salt. The precipitate was filtered and recrystallized with 95% ethanol to obtain 4.6 g of white powdery solid $I_{1r}$ with a yield of 57%; m.p.:

178-179° C.; $[\alpha]^{20}_D$=+32.8° (c=1.00, $CH_3OH$); MS (m/z): 249 $[M_1-H]^-$, 175 $[M_2+H]^+$; $^1H$ NMR (300 MHz, $D_2O$): δ (ppm): 0.75 (t, 3H, $CH_3$, J=6.0 Hz), 1.10-1.30 (m, 4H, $CH_2CH_3$), 1.48-1.66 (m, 2H, $CHCH_2CH_2$), 1.74-1.82 (m, 4H, $CH_2CH_2CHCOOH$), 2.01 (s, 3H, $COCH_3$), 3.13 (t, 2H, $NHCH_2CH_2$, J=6.6 Hz), 3.62 (dd, 1H, $CH_2CHCOOH$, $J_1$=7.5 Hz, $J_2$=6.0 Hz), 6.05 (dd, 1H, $CH_2CHOCOCH_3$, $J_1$=8.1 Hz, $J_2$=6.6 Hz), 7.21-7.38 (m, 4H, ArH); $^{13}C$ NMR (75 MHz, $D_2O$): δ (ppm): 177.5, 174.3, 173.8, 138.1, 136.8, 128.7, 127.7, 126.9, 125.8, 74.9, 54.4, 40.6, 35.2, 27.6, 27.2, 24.5, 23.9, 21.7, 20.7, 13.3.

Example 9: Preparation of Aminoguanidine (R)-2-(1-Acetoxy-n-Pentyl) Benzoate ($I_{7r}$)

2.6 g of (19.2 mmol) aminoguanidine bicarbonate was dissolved in 15 ml of water. Under stirring, the solution was slowly heated to 60° C. After cooling, under the condition of −5 to 30° C., a solution of 4.8 g of (19.2 mmol) (R)-2-(1-acetoxy-n-pentyl)benzoic acid (prepared by the method of Example 8) in 25 mL of absolute ethanol was added. The reaction solution was concentrated to dryness under reduced pressure and recrystallized with 95% ethanol to obtain 1.9 g of white powdery solid $I_7$, with a yield of 43%; m.p.: 109-111° C.; $[\alpha]^{20}_D$=+28.9° (c=1.00, $CH_3OH$); MS (m/z): 249 $[M_1-H]^-$, 75 $[M_2+H]^+$; 1H NMR (300 MHz, $D_2O$): δ (ppm): 0.97 (t, 3H, $CH_3$, J=6.9 Hz), 1.38-1.52 (m, 4H, $CH_2CH_2CH_3$), 1.84-1.99 (m, 2H, $CHCH_2CH_2$), 2.17 (s, 3H, $CHOCOCH_3$), 6.69 (dd, 1H, $CH_2CHOCOCH_3$, $J_1$=8.1 Hz, $J_2$=4.5 Hz), 7.38-7.44 (m, 1H, ArH), 7.56-7.65 (m, 2H, ArH), 8.09-8.12 (m, 1H, ArH); $^{13}C$ NMR (75 MHz, $D_2O$): δ (ppm): 174.4, 158.1, 131.2, 128.8, 128.3, 127.2, 74.9, 61.1, 54.4, 40.5, 27.6, 27.2, 23.9, 21.7, 13.3.

Example 10: Preparation of L-Arginine (S)-2-(1-Acetoxy-n-Pentyl) Benzoate ($I_{1s}$)

(S)-2-(1-acetoxy-n-pentyl)benzoic acid and L-arginine (S)-2-(1-acetoxy-n-pentyl) benzoate ($I_{1s}$) were prepared by a method similar to the method for preparing L-arginine (R)-2-(1-acetoxy-n-pentyl) benzoate ($I_{1r}$) in Example 8.

(S)-2-(1-acetoxy-n-pentyl)benzoic acid: m.p.: 65-66° C.; $[\alpha]^{20}_D$=−37.1° (c=1.00, $CH_3OH$); MS (m/z): 249 $[M_1-H]$; $^1H$ NMR (300 MHz, $CDCl_3$): δ (ppm): 0.97 (t, 3H, $CH_3$, J=6.9 Hz), 1.38-1.52 (m, 4H, $CH_2CH_2CH_3$), 1.84-1.99 (m, 2H, $CHCH_2CH_2$), 2.17 (s, 3H, $CHOCOCH_3$), 6.69 (dd, 1H, $CH_2CHOCOCH_3$, $J_1$=8.1 Hz, $J_2$=4.5 Hz), 7.38-7.44 (m, 1H, ArH), 7.56-7.65 (m, 2H, ArH), 8.09-8.12 (m, 1H, ArH); $^{13}C$ NMR (75 MHz, $CDCl_3$): δ (ppm): 174.4, 131.2, 128.8, 128.3, 127.2, 74.9, 61.1, 54.4, 40.5, 27.6, 27.2, 23.9, 21.7, 13.3.

L-arginine (S)-2-(1-acetoxy-n-pentyl) benzoate ($I_{1s}$): yield 57%, m.p.: 178-179° C.; $[\alpha]^{20}_D$=−25.2° (c=1.00, $CH_3OH$); MS (m/z): 249 $[M_1-H]^-$, 175 $[M_2+H]^+$; $^1H$ NMR (300 MHz, $D_2O$): δ (ppm): 0.76 (t, 3H, $CH_3$, J=6.0 Hz), 1.13-1.33 (m, 4H, $CH_2CH_2CH_3$), 1.52-1.65 (m, 2H, $CHCH_2CH_2$), 1.76-1.83 (m, 4H, $CH_2CH_2CHCOOH$), 2.01 (s, 3H, $COCH_3$), 3.14 (t, 2H, $NHCH_2CH_2$, J=6.9 Hz), 3.64 (dd, 1H, $CH_2CHCOOH$, $J_1$=7.5 Hz, $J_2$=6.0 Hz), 6.05 (dd, 1H, $CH_2CHOCOCH_3$, $J_1$=8.1 Hz, $J_2$=6.6 Hz), 7.24-7.38 (m, 4H, ArH); $^{13}C$ NMR (75 MHz, $D_2O$): δ (ppm): 177.5, 174.3, 173.8, 138.1, 136.8, 128.7, 127.7, 126.9, 125.8, 74.9, 54.4, 40.6, 35.2, 27.6, 27.2, 24.5, 23.9, 21.7, 20.7, 13.3.

Example 11: Preparation of Aminoguanidine (S)-2-(1-Acetoxy-n-Pentyl) Benzoate ($I_{7s}$)

Aminoguanidine (S)-2-(1-acetoxy-n-pentyl) benzoate ($I_{7s}$) with a yield of 43% was prepared by a method similar to the method for preparing aminoguanidine (R)-2-(1-acetoxy-n-pentyl) benzoate ($I_{7r}$) in Example 9; m.p.: 109-111° C.; $[\alpha]^{20}_D$=−30.2° (c=1.00, $CH_3OH$); MS (m/z): 249 $[M_1-H]^-$, 75 $[M_2+H]^+$; $^1H$ NMR (300 MHz, $D_2O$): δ (ppm): 0.97 (t, 3H, $CH_3$, J=6.9 Hz), 1.38-1.52 (m, 4H, $CH_2CH_2CH_3$), 1.84-1.99 (m, 2H, $CHCH_2CH_2$), 2.17 (s, 3H, $CHOCOCH_3$), 6.69 (dd, 1H, $CH_2CHOCOCH_3$, $J_1$=8.1 Hz, $J_2$=4.5 Hz), 7.38-7.44 (m, 1H, ArH), 7.56-7.65 (m, 2H, ArH), 8.09-8.12 (m, 1H, ArH); $^{13}C$ NMR (75 MHz, $D_2O$): δ (ppm): 174.4, 158.1, 131.2, 128.8, 128.3, 127.2, 74.9, 61.1, 54.4, 40.5, 27.6, 27.2, 23.9, 21.7, 13.3.

Example 12: Preparation of L-Arginine (R/S)-2-(1-Hydroxy-n-Pentyl) Benzoate (AHPB)

Under the condition of −30 to −5° C., a solution of 1.9 g of (10.3 mmol) arginine in water (20 ml) was added dropwise slowly to a solution of (R/S)-2-((1-hydroxy-n-pentyl) benzoic acid (2.2 g, 10.5 mmol) in ethanol (20 ml), and the reaction was performed under stirring for 2 h. The reaction solution was concentrated to dryness under reduced pressure, and an appropriate amount of acetone was added. The precipitated white solid was filtered and dried in vacuum to obtain 3.2 g of AHPB. The solid is able to absorb moisture very easily, and the yield is 79%; MS (m/z): 207 $[M_1-H]^-$, 175 $[M_2+H]^+$; $^1H$ NMR (300 MHz, MeOD): δ 0.89 (t, 3H, $CH_3$, J=7.0 Hz), 1.30-1.36 (m, 4H, $CH_2CH_2CH_3$), 1.74-1.81 (m, 4H, $CH_2CH_2CHCOOH$), 1.82-1.92 (m, 2H, $CHCH_2CH_2$), 3.21 (t, 2H, $NHCH_2CH_2$), 3.57 (dd, 1H, $CH_2CHCOOH$, $J_1$=7.5 Hz, $J_2$=6.0 Hz), 4.86 (dd, 1H, $CH_2CHOH$, $J_1$=8.1 Hz, $J_2$=4.5 Hz), 7.21-7.32 (m, 1H, ArH), 7.33-7.38 (m, 2H, ArH), 7.57-7.64 (m, 1H, ArH); $^{13}C$ NMR (75 MHz, MeOD): δ 177.1, 160.9, 145.7, 141.9, 132.2, 132.1, 132.0, 130.3, 130.2, 129.9, 57.6, 43.9, 40.6, 31.8, 31.6, 27.8, 25.7, 16.5.

Example 13: Solubility Test

Test method: 10 mg of a test sample (solid was ground into fine powder) was weighed and added to a certain amount of solvent at 25±2° C. (the temperature of a water bath is controlled at 25° C.), and the solution was shaken vigorously for 30 s every 5 min. The dissolution was observed within 30 min. When there were no visible solute particles or droplets, the test sample was regarded as completely dissolved.

Test Result:

TABLE 1

Saturated solubility of compounds in water*

| Sample name | Saturated solubility in $H_2O$ (mg/mL) | | |
|---|---|---|---|
| | $I_{1s}$ | PHPB | (S)-NBP |
| Dissolved sample amount | 133.80 | 148.30 | 0.72 |
| | 134.24 | 148.04 | 0.71 |
| | 138.23 | 145.97 | 0.35 |
| | 138.40 | 145.98 | 0.36 |
| Mean | 136.17 | 147.07 | 0.54 |
| SD | 2.49 | 1.27 | 0.21 |
| RSD | 1.83 | 0.86 | 38.90 |

*$I_{1s}$: L-arginine (S)-2-(1-acetoxy-n-pentyl) benzoate; PHPB: potassium (R/S)-2-(1-hydroxy-n-pentyl) benzoate; (S)-NBP: (S)-butylphthalide.

Conclusion: The water solubility of compound $I_{1s}$ is equivalent to that of PHPB, and is significantly better than S—NBP.

Example 14: Preliminary Stability

Test Method:

2018 Jun. 25 10 mg of the $I_{1s}$ sample was precisely weighed and added into a colorimetric tube, and diluted with a solvent (water/methanol) to 10 mL to prepare a stock solution with a concentration of 1 mg/mL. For each sample test, the stock solution was taken and diluted freshly.

2018 Jun. 29 200 μL of the stock solution was pipetted, 3800 μL of a mobile phase in the initial ratio was added, and 10 μL of a test sample with a concentration of 50 μg/mL was prepared for injection and analysis.

2018 Jul. 2 200 μL of the stock solution was pipetted, 3800 μL of a mobile phase in the initial ratio was added, and 10 μL of a test sample with a concentration of 50 μg/mL was prepared for injection and analysis.

2018 Jul. 7 200 μL of the stock solution was pipetted, 3800 μL of a mobile phase in the initial ratio was added, and 10 μL of a test sample with a concentration of 50 μg/mL was prepared for injection and analysis.

Figure 2:
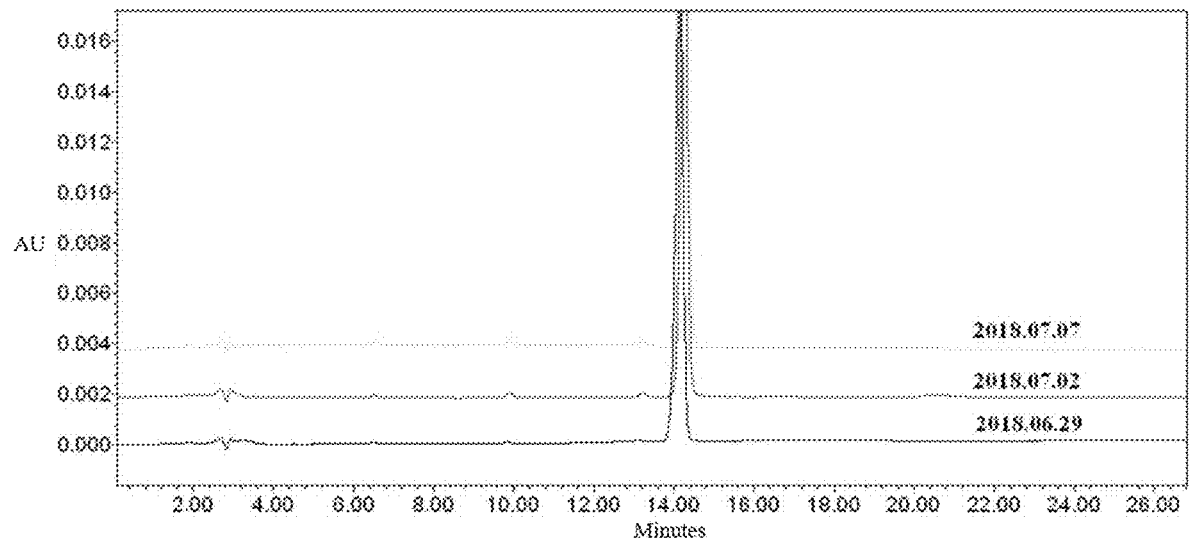
FIG. 2 is a sample solution stability analysis spectrogram of compound $I_{1s}$ in $CH_3OH$.

Test Result:

The stability analysis spectrograms of the compound $I_{1s}$ on 2018 Jun. 29, 2018 Jul. 2, and 2018 Jul. 7 are shown in FIG. 1 and FIG. 2, wherein FIG. 1 shows the stability of the sample solution in $H_2O$, and FIG. 2 shows the stability of the sample solution in $CH_3OH$. Conclusion: The compound $I_{1s}$ was basically stable in water and methanol during the test period (2018 Jun. 29, 2018 Jul. 2, and 2018 Jul. 7).

tube was inserted into the common carotid artery to collect blood. The blood was injected into a siliconized centrifuge tube containing 1/10 by volume of a 3.8% sodium citrate solution. The blood was gently mixed with the anticoagulant uniformly, and centrifuged at 1000 rpm for 15 min. The upper beige suspension was pipetted to obtain the platelet-rich plasma (PRP). The remaining plasma was centrifuged at 3000 rpm for 15 min, and the supernatant was pipetted to prepare the platelet-poor plasma (PPP). The PRP was adjusted with the PPP to make the platelet count at $1 \times 10^8$/mL.

Determination of Platelet Aggregation Rate by Turbidimetry at 37° C.

260 μL of platelet-rich plasma (PRP) was added into a turbidimetric tube. Then 10 μL of test compounds with different concentrations, positive control drugs or normal saline were separately added, and the plasma was incubated at 37° C. for 5 min. Then 30 μL of inducers were added in sequence. The final concentration of an inducer ADP is 10 μM, and the final concentration of an inducer AA is 1 mM. The maximum aggregation rate within 5 min was determined by an aggregometer, and the inhibition rate of the drugs on platelet aggregation was calculated. Inhibition rate of platelet aggregation (IRPA)=(platelet aggregation rate of the control group−platelet aggregation rate of the experimental group)/platelet aggregation rate of the control group× 100%.

Test Result:

TABLE 2

Inhibitory activity of the compounds of the disclosure on ADP and AA induced platelet aggregation in rabbits*

| | $IC_{50}$ (mM) | | | $IC_{50}$ (mM) | |
|---|---|---|---|---|---|
| Compd. | ADP (10 μM) | AA (1 mM) | Compd. | ADP (10 μM) | AA (1 mM) |
| Aspirin | 0.78 ± 0.05 | 0.16 ± 0.01 | $I_1$ | 0.74 ± 0.09 | 0.18 ± 0.03 |
| (R/S)-NBP | 1.36 ± 0.13 | 0.60 ± 0.07 | $I_2$ | 0.65 ± 0.04 | 0.19 ± 0.02 |
| (S)-NBP | 1.29 ± 0.11 | 0.50 ± 0.04 | $I_3$ | 1.26 ± 0.07 | 0.52 ± 0.03 |
| (R)-NBP | 1.60 ± 0.15 | 0.66 ± 0.07 | $I_4$ | 0.82 ± 0.05 | 0.17 ± 0.07 |
| L-arginine | 5.86 ± 0.69 | 5.13 ± 0.65 | $I_5$ | 1.15 ± 0.08 | 0.46 ± 0.03 |
| (R/S)-APB | 0.81 ± 0.04 | 0.47 ± 0.04 | $I_6$ | 0.77 ± 0.05 | 0.14 ± 0.01 |
| (S)-APB | 0.79 ± 0.08 | 0.43 ± 0.05 | $I_7$ | 1.18 ± 0.06 | 0.28 ± 0.07 |
| (R)-APB | 0.76 ± 0.07 | 0.19 ± 0.02 | $I_{1r}$ | 0.73 ± 0.07 | 0.18 ± 0.03 |
| (S)-APB + L-arginine | 0.75 ± 0.05 | 0.37 ± 0.03 | $I_{7r}$ | 0.94 ± 0.05 | 0.21 ± 0.01 |
| AHPB | 0.98 ± 0.21 | 0.34 ± 0.04 | $I_{1s}$ | 0.72 ± 0.08 | 0.16 ± 0.02 |
| PHPB | 0.96 ± 0.07 | 0.35 ± 0.09 | $I_{7s}$ | 0.68 ± 0.03 | 0.12 ± 0.01 |

*ASP: Aspirin; (R/S)-, (R)-, and (S)-NBP: (R/S)-, (R)-, and (S)-butylphthalide respectively; L-Arg: L-arginine; (R/S)-, (R)-, and (S)-APB: (R/S)-, (R)-, and (S)-2-(1-acetoxy-n-pentyl)benzoic acid respectively; AHPB: L-arginine (R/S)-2-(1-hydroxy-n-pentyl) benzoate; PHPB: potassium (R/S)-2-(1-hydroxy-n-pentyl) benzoate; $I_1$, $I_7$, and $I_{1s}$: L-arginine (R/S)-, (R)-, and (S)-2-(1-acetoxy-n-pentyl) benzoate respectively; compounds $I_2$-$I_7$, $I_{7r}$, and $I_{7s}$: see Examples 2-11.

Example 15: In Vitro Anti-Platelet Aggregation Activity

Test animals: New Zealand breed white rabbits, half male and half female, 1.8-2.2 kg, purchased from Beijing Vital River Laboratory Animal Technology Co., Ltd., and raised in a clean and hygienic SPF animal room with indoor temperature controlled at 25±2° C. and a relative humidity of 60-75%. The animals were used for experiments after 1 week.

Test Method:

Preparation of Platelet-Rich Plasma (PRP) and Platelet-Poor Plasma (PPP)

The rabbits fasted for 12-18 h were anesthetized by intraperitoneal injection with a 20% urethane solution. The common carotid artery was separated, and a polyethylene

Example 16: Antithrombotic Activity

1. Effect on Bleeding Time in Mice after Tail Cutting

Test Animals:

SPF Kunming mice, weighing 18-22 g, purchased from Beijing Vital River Laboratory Animal Technology Co., Ltd., having a certificate number of SCXK (Beijing) 2010-0002, raised in an SPF animal room with indoor temperature controlled at 23±2° C., and allowed to freely eat and drink. The day and night time was 12 h/12 h.

Test Method:

48 Kunming mice, weighing 18-22 g, half male and half female, were randomly divided into 8 groups: negative control group, ASP group, clopidogrel group, ASP+clopidogrel group, $I_{1s}$ group, $I_{1s}$+Aspirin group, $I_{1s}$+clopidogrel group, and $I_{1s}$+aspirin+clopidogrel group. The administration dose level of the positive drug groups and the test drug groups was 5 mg/kg, and the same amount of normal saline was given to the negative control group. All mice were administered for 14 consecutive days orally once a day. One hour after the last dose, the mice were anesthetized with 1-2% isoflurane, and the tails were cut for 5 mm. The tips of the tails were absorbed dry with filter paper every 30 seconds until the bleeding stopped naturally. Bleeding time is defined as the interval between the start and stop of bleeding.

Test Result:

TABLE 3

Bleeding result*

| Compd. | Bleeding time (min) |
| --- | --- |
| Control group | 14.28 ± 0.50 |
| Aspirin | 22.52 ± 1.31 |
| Clopidogrel | 25.28 ± 0.48 |
| Aspirin + clopidogrel | 27.36 ± 1.36 |
| $I_{1s}$ | 25.31 ± 1.01 |
| $I_{1s}$ + aspirin | 27.85 ± 1.25 |
| $I_{1s}$ + clopidogrel | 29.69 ± 1.33 |
| $I_{1s}$ + aspirin + clopidogrel | 29.77 ± 1.18 |

*$I_{1s}$: L-arginine (S)-2-(1-acetoxy-n-pentyl) benzoate.

Conclusion: The bleeding time of mice under the action of compound $I_{1s}$ is equivalent to that of the positive drug clopidogrel, and longer than that of aspirin, suggesting that $I_{1s}$ has a better anticoagulation effect than aspirin.

2. Effect on Arteriovenous Bypass Thrombosis in Rats

Test Animals:

Male SD rats, weighing 250-280 g, purchased from Beijing Vital River Laboratory Animal Technology Co., Ltd., raised in an SPF breeding environment with indoor temperature controlled at 23±2° C., and allowed to freely eat and drink. The total number of the animals is 64.

Test Groups:

Model group: injected with the same volume of normal saline (containing 1% DMSO) through the tail vein, and administered continuously for 7 days. The test was started 2 h after the last dose (n=8).

Test drug groups: Aspirin group, S—NBP(S-butylphthalide) group, Edaravone group, PHPB(potassium (R/S)-2-(1-hydroxy-n-pentyl) benzoate) group, $I_1$ group, $I_{1r}$ group, and $I_{1s}$ group. The dose of all drugs was 10 mg/kg/day. The drugs were formulated into normal saline solutions containing 1% DMSO, and injected through the tail vein for 7 consecutive days. The test was started 2 hours after the last dose (n=8).

Test Method:

The rats were intraperitoneally injected with a 3% pentobarbital sodium solution (30 mg/kg). After anesthesia, the rats were immobilized in the supine position, and a median cervical incision was made to separate the right common carotid artery and left external jugular vein. A 6 cm long suture was put in the middle of a polyethylene tube (the suture needs to be weighed before being put in the tube), and the polyethylene tube was filled with heparin saline (50 U/mL). The polyethylene tube was inserted into the separated blood vessels to make the artery and vein form a loop. After 15 min of circulation of the blood flow, the suture was taken out, and the suture with thrombus was collected and weighed immediately. Then, after the suture was dried at room temperature for 24 h, the dry weight was determined. The total weight minus the weight of the suture was the wet weight of the thrombus, and the dry weight minus the weight of the suture was the dry weight of the thrombus. Thrombosis inhibition rate (%)=(wet/dry weight of thrombus in the model group−wet/dry weight of thrombus in the administration group)÷wet/dry weight of thrombus in the model group×100%

Figure 3A:
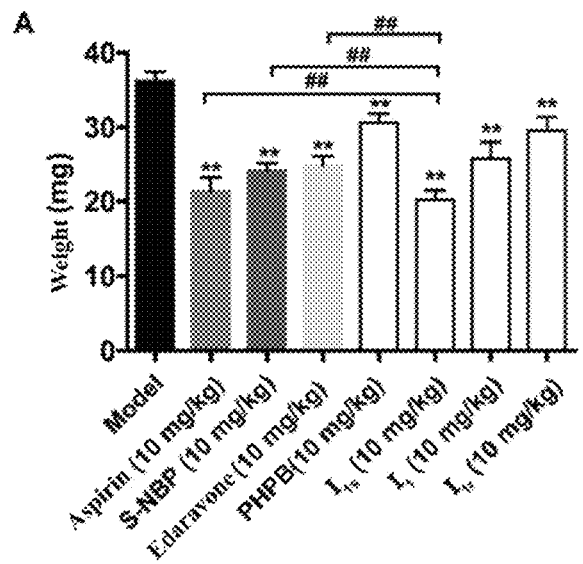
FIG. 3A shows the effects of test compounds on arteriovenous bypass thrombosis in rats (Wet weight of thrombus).
Figure 3B:
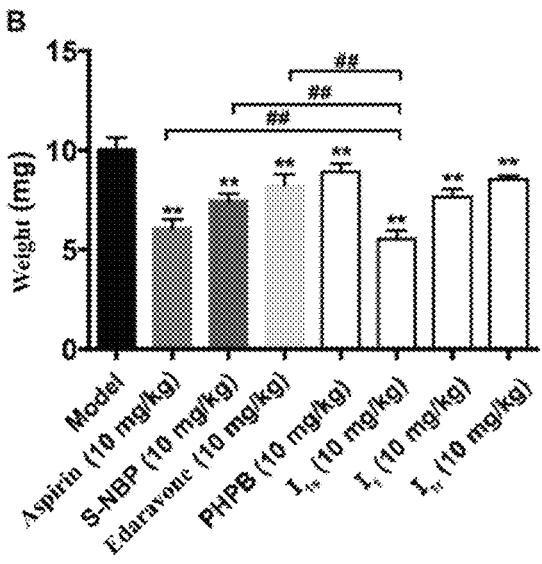
FIG. 3B shows the effects of test compounds on arteriovenous bypass thrombosis in rats (Dry weight of thrombus).
Figure 4A:
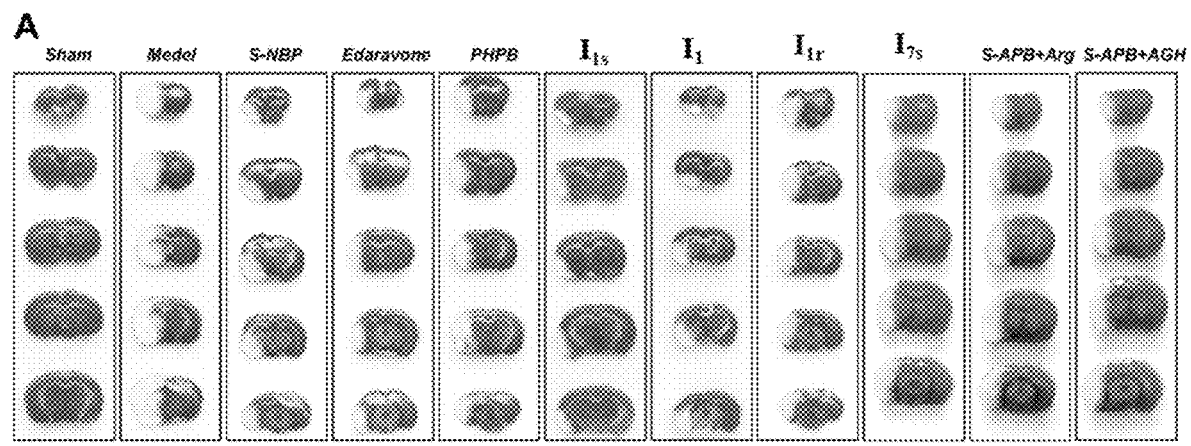
FIG. 4A shows the effects of compounds on infarct volume, cerebral edema and nerve defects in MCAO rats (TTC staining and brain imaging analysis).
Figure 4B:
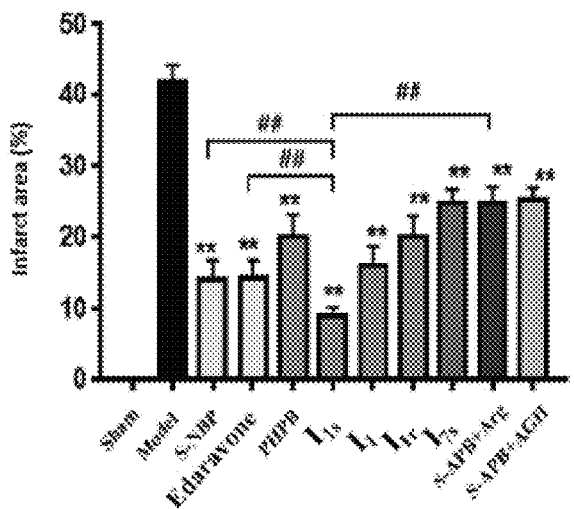
FIG. 4B shows the effects of compounds on infarct volume, cerebral edema and nerve defects in MCAO rats (Infarct volume data).
Figure 4C:
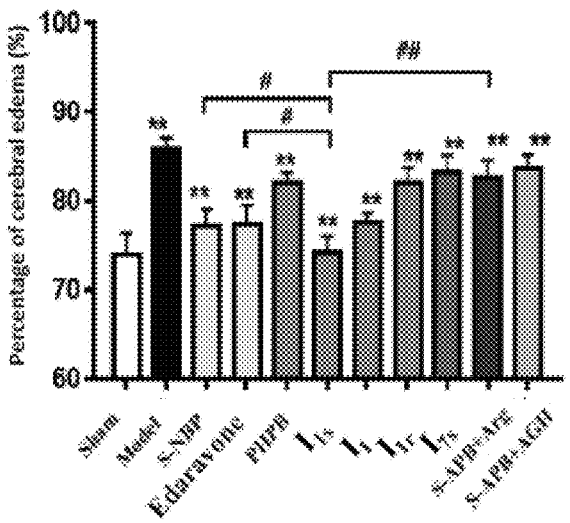
FIG. 4C shows the effects of compounds on infarct volume, cerebral edema and nerve defects in MCAO rats (Brain water content).
Figure 4D:
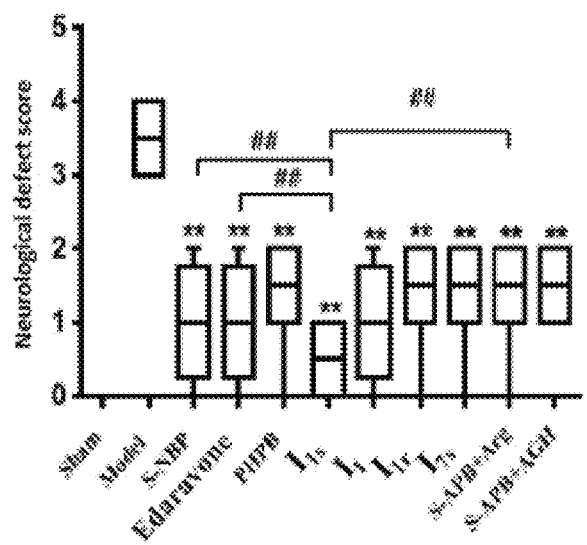
FIG. 4D shows the effects of compounds on infarct volume, cerebral edema and nerve defects in MCAO rats (Nerve defect assessment).
Figure 5A:
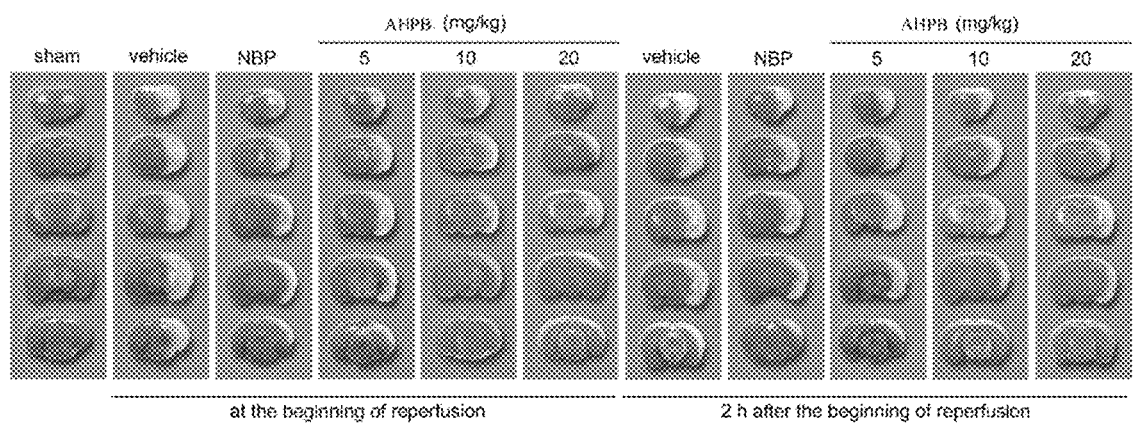
FIG. 5A shows the effects of the compound AHPB on infarct volume, cerebral edema and nerve defects in MCAO rats (TTC staining and brain imaging analysis).
Figure 5B:
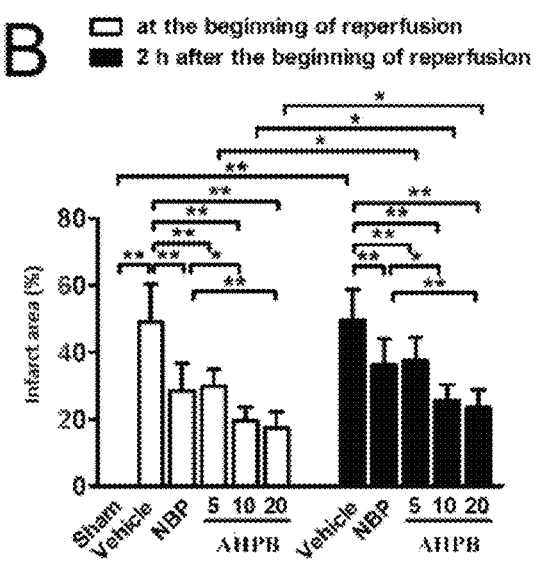
FIG. 5B shows the effects of the compound AHPB on infarct volume, cerebral edema and nerve defects in MCAO rats (Infarct volume data).
Figure 5C:
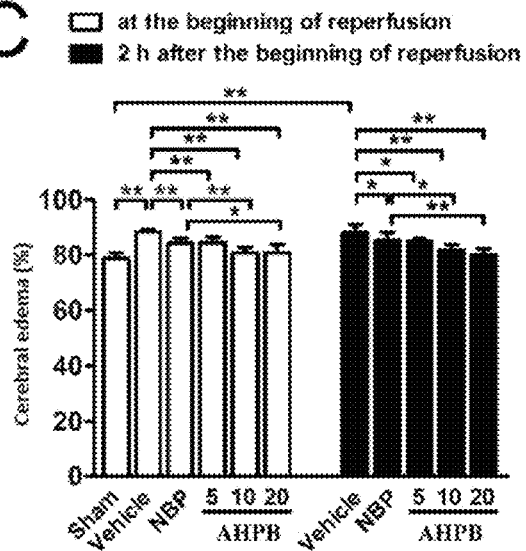
FIG. 5C shows the effects of the compound AHPB on infarct volume, cerebral edema and nerve defects in MCAO rats (Brain water content).
Figure 5D:
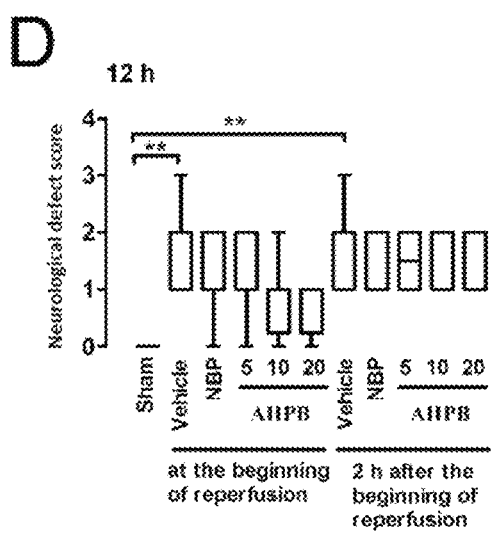
FIG. 5D shows the effects of the compound AHPB on infarct volume, cerebral edema and nerve defects in MCAO rats (Nerve defect assessment 12 h after reperfusion).
Figure 5E:
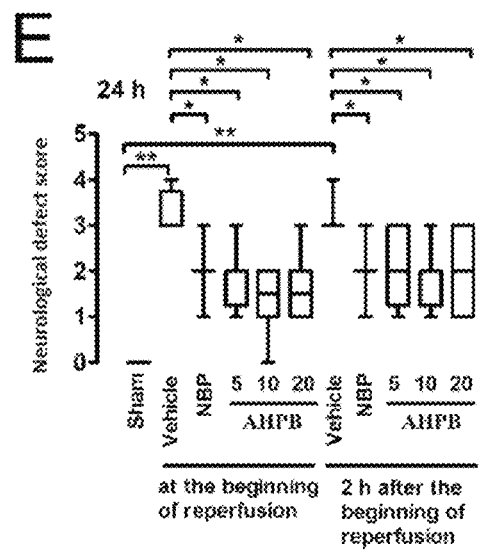
FIG. 5E shows the effects of the compound AHPB on infarct volume, cerebral edema and nerve defects in MCAO rats (Nerve defect assessment 24 h after reperfusion).

Test Result:

See FIG. 3 and Table 4. In FIG. 3: (A) Wet weight of thrombus; (B) Dry weight of thrombus; Data are expressed as mean±SD (n=8), *P<0.05, **P<0.01; Compared with the $I_{1s}$ group: #P<0.05, ##P<0.01.

TABLE 4

Effects of test compounds on arteriovenous bypass thrombosis in rats $^\Theta$

| Compd. | Number of animals | Wet weight of thrombus | Inhibition rate (%) | Dry weight of thrombus | Inhibition rate (%) |
| --- | --- | --- | --- | --- | --- |
| Model group | 8 | 36.21 ± 1.16 | | 10.04 ± 0.62 | |
| Aspirin | 8 | 21.46 ± 1.76**## | 40.74## | 6.06 ± 0.46**## | 39.67## |
| S-NBP | 8 | 24.18 ± 1.02**## | 33.24## | 7.44 ± 0.37**## | 25.95## |
| Edaravone | 8 | 24.95 ± 1.20**## | 31.12## | 8.23 ± 0.53**## | 18.05## |
| PHPB | 8 | 30.64 ± 10.21** | 15.39 | 8.90 ± 0.45** | 11.32 |
| $I_{1s}$ | 8 | 20.23 ± 1.25** | 44.14 | 5.52 ± 0.44** | 45.02 |
| $I_1$ | 8 | 25.81 ± 2.20** | 28.72 | 7.64 ± 0.40** | 23.94 |
| $I_{1r}$ | 8 | 29.56 ± 1.84** | 18.37 | 8.51 ± 0.18** | 15.23 |

*P < 0.05,
**P < 0.01,
P < 0.05,
P < 0.01.
$^\Theta$ S-NBP: S-butylphthalide; PHPB: potassium (R/S)-2-(1-hydroxy-n-pentyl) benzoate; $I_1$, $I_r$, and $I_{1s}$: (R/S)-, (R)-, and L-arginine (S)-2-(1-acetoxy-n-pentyl) benzoate respectively.

Conclusion: Compared with the model group, 10 mg/kg of aspirin, S—NBP, Edaravone, PHPB, $I_{1s}$, $I_1$ and $I_{1r}$ can significantly reduce the wet and dry weight of thrombus in rats (p<0.01, p<0.01, p<0.01, p<0.01, p<0.01, p<0.01, p<0.01). The inhibitory effect of compound $I_{1s}$ on thrombosis in rats is significantly stronger than the same dose of aspirin, S—NBP and Edaravone (p<0.01, p<0.01, p<0.01).

Example 17: Effects on Cerebral Infarction, Cerebral Edema and Nerve Function of Rats with Focal Cerebral Ischemia Test Animals:

SPF SD rats, weighing 200-220 g, half male and half female, purchased from Beijing Vital River Laboratory Animal Technology Co., Ltd., raised in an SPF breeding environment with indoor temperature controlled at 23±2° C., and allowed to freely eat and drink. The total number of the animals was 88.

Test Groups:

Sham operation group: equal volume of normal saline (containing 1% DMSO) (iv. 3 days), TTC, cerebral edema and neurological function score (n=8);

Model group: equal volume of normal saline (containing 1% DMSO) (iv. 3 days, administration 2 h after reperfusion), TTC, cerebral edema and neurological function score (n=8);

S—NBP (S-butylphthalide) group, Edaravone group, and PHPB (potassium R/S-2-(1-hydroxy-n-pentyl) benzoate) group: 10 mg/kg/day (iv. 3 days, administration 2 h after reperfusion), TTC, cerebral edema and neurological function score (n=8);

$I_1$, $I_r$, $I_{1s}$, and $I_{7s}$ groups: 10 mg/kg/day (iv. 3 days, administration 2 h after reperfusion), TTC, cerebral edema and neurological function score (n=8);

Equimolar S-APB (S-2-(1-acetoxy-n-pentyl)benzoic acid)+Arg (arginine) combined administration group: (S-APB 5.89 mg/kg+Arg 4.10 mg/kg)/day (iv. 3 days, administration 2 h after reperfusion), TTC, cerebral edema and neurological function score (n=8);

Equimolar S-APB+AGH (aminoguanidine hydrochloride) combined administration group: (S-APB 7.72 mg/kg+ AGH 3.41 mg/kg)/day (iv. 3 days, administration 2 h after reperfusion), TTC, cerebral edema and neurological function score (n=8).

Test Method:

The middle cerebral arteries of the rats were blocked by a suture-occluded method, and reperfused after 2 h. 2 h after perfusion, the rats were injected with S—NBP, Edaravone, PHPB, $I_1$, $I_{1r}$, $I_{1s}$, $I_{7s}$, equimolar combination of S-APB and arginine, equimolar combination of S-APB and aminoguanidine hydrochloride, and an equal volume of normal saline (containing 1% DMSO) in the tail vein. All drugs were formulated into normal saline solutions containing 1% DMSO for administration, and the duration of administration was controlled at approximately 1 min. The drugs were administered for the first time 2 h after reperfusion, and were administered once every 24 h for a total of 3 times. 2 h after the last administration, the neurological defect scores were firstly obtained, and then the rats of each group were sacrificed. The whole brains were taken out and weighed (wet weight), TTC stained, and dried to determine the effects of the compounds on cerebral infarction and cerebral edema.

Neurological Defect Score 2 h after the last administration, the neurological defects of the animals were graded and scored by the Longa's method. The criteria are as follows: 0 point: no neurological signs are observed; 1 point: when the animal is suspended with its tail being lifted, the operation contralateral forelimb of the animal exhibits wrist and elbow flexion, shoulder internal rotation, elbow abduction, and closeness to the chest wall; 2 points: when the animal is placed on a smooth surface and the shoulder of the operation side is pushed to the opposite side, the resistance decreases; 3 points: when the animal walks freely, the animal turns or turns around to the opposite side of the operation; and 4 points: the animal exhibits flaccid paralysis, and no spontaneous movement of the limbs are observed.

TTC Staining

After the neurobehavioral examination was completed, four coronal incisions were made on the whole brains of the rats on the optic chiasma and 2 mm anteroposterior positions of the optic chiasma. After the whole brains were cut into five slices, the brain slices were quickly placed in 5 ml of phosphate buffer solution containing 2% TTC, and incubated at 37° C. in the dark. In the incubation process, the brain slices were turned once every 5 min. After 10 min of incubation, the brain slices were taken out and pictures were taken with a digital camera (Olympus C-4000, Japan). Then the pale area (infarct area) and non-pale area (normal area) were separated by using ophthalmic forceps, and the infarct percentage was calculated by Image pro-plus 6.0 as follows:

Infarct percentage (%)=weight of pale area/(weight of pale area+weight of non-pale area)×100%;

Infarction area inhibition rate (%)=(infarct percentage of model group (%)−infarct percentage of administration group (%))/infarct percentage of model group (%)×100%.

The stained brain tissue was dried in an oven at 105° C., and weighed (dry weight) after 24 h. The calculation formula of brain water content is as follows:

Water content of brain tissue (%)=(wet weight of brain tissue−dry weight of brain tissue)/wet weight of brain tissue×100%;

Cerebral edema rate (%)=water content of brain tissue of each group (%)−water content of brain tissue of sham operation group (%)/water content of brain tissue of sham operation group (%)×100%;

Inhibition rate of cerebral edema (%)=(rate of cerebral edema of model group (%)−rate of cerebral edema of administration group (%))/rate of cerebral edema of model group (%)×100%.

Test Result:

The effects of the compounds on the infarct volume, cerebral edema and nerve defect of MCAO rats are shown in FIG. 4, Table 5 and Table 6. In FIG. 4: (A) TTC staining and brain imaging analysis; B) Infarct volume data; (C) Brain water content; and (D) Nerve defect assessment. Except for the median value for neurological defect score (n=8), other data are expressed as mean±SD. *$P<0.05$, **$P<0.01$; #$P<0.05$, ##$P<0.01$.

TABLE 5

Effects of compounds on cerebral infarct volume*

| Compd. | Infarct volume (%) | Inhibition rate of infarct volume (%) |
|---|---|---|
| Sham operation group | 0 | / |
| Model group | 41.85 ± 2.43 | / |
| S-NBP | 14.18 ± 2.69 | 66.12 |
| Edaravone | 14.29 ± 2.58 | 65.85 |
| PHPB | 20.23 ± 3.02 | 51.66 |
| $I_{1s}$ | 9.12 ± 1.18 | 78.21 |
| $I_1$ | 16.11 ± 2.74 | 61.50 |
| $I_{1r}$ | 20.14 ± 2.95 | 51.89 |
| $I_7s$ | 24.83 ± 2.02 | 40.67 |
| S-APB + Arg | 24.93 ± 2.2 | 40.43 |
| S-APB + AGH | 25.27 ± 1.80 | 39.61 |

*S-NBP: S-butylphthalide; PHPB: potassium R/S-2-(1-hydroxy-n-pentyl) benzoate; $I_1$, $I_r$, and $I_{1s}$: L-arginine R/S-, R-, and S-2-(1-acetoxy-n-pentyl) benzoate respectively; $I_7S$: aminoguanidine S-2-(1-acetoxy-n-pentyl) benzoate; S-APB: S-2-(1-acetoxy-n-pentyl)benzoic acid; Arg: L-arginine; AGH: aminoguanidine hydrochloride.

TABLE 6

Effects of compounds on cerebral edema*

| Compd. | Cerebral edema (%) | Inhibition rate of cerebral edema (%) |
|---|---|---|
| Sham operation group | 0 | / |
| Model group | 16.04 ± 2.82 | 0 |
| S-NBP | 4.45 ± 4.58 | 72.28 |
| Edaravone | 4.49 ± 4.84 | 72.01 |

TABLE 6-continued

Effects of compounds on cerebral edema*

| Compd. | Cerebral edema (%) | Inhibition rate of cerebral edema (%) |
|---|---|---|
| PHPB | 10.71 ± 3.55 | 33.23 |
| $I_{1s}$ | 0.18 ± 3.96 | 98.85 |
| $I_1$ | 4.97 ± 3.30 | 69.00 |
| $I_{1r}$ | 10.72 ± 4.19 | 33.20 |
| $I_{7s}$ | 12.34 ± 4.57 | 23.07 |
| S-APB + Arg | 11.54 ± 4.57 | 28.05 |
| S-APB + AGH | 12.90 ± 4.86 | 19.58 |

*S-NBP: S-butylphthalide; PHPB: potassium R/S-2-(1-hydroxy-n-pentyl) benzoate; $I_1$, $I_{1r}$, and $I_{1s}$: L-arginine R/S-, R-, and S-2-(1-acetoxy-n-pentyl) benzoate respectively; $I_{7s}$: aminoguanidine S-2-(1-acetoxy-n-pentyl) benzoate; S-APB: S-2-(1-acetoxy-n-pentyl)benzoic acid; Arg: L-arginine; AGH: aminoguanidine hydrochloride.

Conclusion: L-arginine S-2-(1-acetoxy-n-pentyl) benzoate ($I_{1s}$) has the most significant inhibitory effects on cerebral infarction and cerebral edema in rats and significant neurological improvement effects on rats with focal cerebral ischemia 2 h after reperfusion, is better than the equimolar dose of S-APB and L-arginine in combination, and is better than the same dose of S—NBP, PHPB and Edaravone.

The method for testing the effects of L-arginine (R/S)-2-(1-hydroxy-n-pentyl) benzoate (AHPB) on cerebral infarction, cerebral edema and neurological function of rats with focal cerebral ischemia is the same as above, and the results are as follows:

The effect of the compound AHPB on the infarct volume, cerebral edema and nerve defect in MCAO rats is shown in FIG. 5, Table 7 and Table 8. In FIG. 5: (A) TTC staining and brain imaging analysis; B) Infarct volume data; (C) Brain water content; (D) Nerve defect assessment 12 h after reperfusion; (E) Nerve defect assessment 24 h after reperfusion. Except for the median value for neurological defect score (n=8), other data are expressed as mean±SD. *P<0.05, **P<0.01.

TABLE 7

Effect of L-arginine (R/S)-2-(1-hydroxy-n-pentyl) benzoate (AHPB) on infarct volume*

| Administration method | Compd. (dose) | Infarct volume (%) | Inhibition rate of infarct volume (%) |
|---|---|---|---|
| / | Sham operation group | 0 | / |
| At the beginning of reperfusion, iv administration | Model group | 49.19 ± 11.16 | / |
| | NBP (5 mg/kg) | 28.55 ± 8.25 | 41.96 |
| | AHPB (5 mg/kg) | 29.98 ± 4.99 | 39.06 |
| | AHPB (10 mg/kg) | 19.83 ± 3.95 | 59.69 |
| | AHPB (20 mg/kg) | 17.71 ± 4.65 | 64.00 |
| 2 h after the beginning of reperfusion, iv administration | Model group | 49.61 ± 9.14 | / |
| | NBP (5 mg/kg) | 36.50 ± 7.58 | 26.43 |
| | AHPB (5 mg/kg) | 37.54 ± 6.94 | 24.34 |
| | AHPB (10 mg/kg) | 25.70 ± 4.75 | 48.19 |
| | AHPB (20 mg/kg) | 23.56 ± 5.29 | 52.51 |

*NBP: butylphthalide; AHPB: L-arginine (R/S)-2-(1-hydroxy-n-pentyl) benzoate.

TABLE 8

Effect of L-arginine (R/S)-2-(1-hydroxy-n-pentyl) benzoate (AHPB) on cerebral edema*

| Administration method | Compd. (dose) | Cerebral edema (%) | Inhibition rate of cerebral edema (%) |
|---|---|---|---|
| / | Sham operation group | 0 | / |
| At the beginning of reperfusion, iv administration | Model group | 9.71 ± 1.39 | / |
| | NBP (5 mg/kg) | 5.80 ± 1.83 | 40.21 |
| | AHPB (5 mg/kg) | 5.94 ± 2.45 | 38.82 |
| | AHPB (10 mg/kg) | 2.01 ± 2.91 | 79.34 |
| | AHPB (20 mg/kg) | 2.08 ± 4.58 | 78.57 |
| 2 h after the beginning of reperfusion, iv administration | Model group | 9.44 ± 4.17 | / |
| | NBP (5 mg/kg) | 6.72 ± 4.05 | 28.80 |
| | AHPB (5 mg/kg) | 6.50 ± 1.86 | 31.12 |
| | AHPB (10 mg/kg) | 3.03 ± 2.87 | 67.94 |
| | AHPB (20 mg/kg) | 1.64 ± 3.36 | 82.57 |

*NBP: butylphthalide; AHPB: L-arginine (R/S)-2-(1-hydroxy-n-pentyl) benzoate.

Conclusion: At the same time of reperfusion or 2 h after perfusion, intravenous injection of low-dose (5 mg/kg) AHPB has no significant difference in the effects of improving cerebral infarction, cerebral edema and neurological function in rats with focal cerebral ischemia compared with NBP (5 mg/kg), while middle and high doses (10, 20 mg/kg) of AHPB are better than NBP (5 mg/kg) in improving cerebral infarction and cerebral edema, and are equivalent to NBP (5 mg/kg) in improving the neurological function.

Example 18: Pharmacokinetics

Test Animals:

12 clean SD male rats, provided by Qinglongshan Animal Breeding Farm in Jiangning District, Nanjing. The production license number is SCXK (Jiangsu) 2017-0001. The body weight of the rats ranges from 180 to 220 g. The rats were used after being raised in the laboratory of an experimental animal center for 2 days after purchase, fasted for 12 hours before administration and 6 hours after administration, and were allowed to freely drink during the test period.

Test Method:

The rats were injected with L-arginine (S)-2-(1-acetoxy-n-pentyl) benzoate ($I_{1s}$) (25 mg/kg) in the tail veins, and blood was taken from the fundus venous plexus of the rats at various time points. The concentration of the original drugs and metabolites in the rat blood were determined by LC-MS/MS, and WinNonlin pharmacokinetics professional software and a statistical moment method were used for calculation to obtain the corresponding pharmacokinetic parameters.

Test Result:

1. The compound $I_{1s}$ was rapidly metabolized into corresponding carboxylic acid and L-arginine in the body. The active metabolite (S)-2-(1-acetoxy-n-pentyl)benzoic acid (abbreviated as metabolite M2), (S)-2-(1-hydroxy-n-pentyl) benzoic acid (the deacetylation product of M2) (M3) and (S)—NBP (M4) were detected in the plasma 2 min after administration, wherein M2 and M4 were the main metabolites, and the concentration of the intermediate metabolite M3 was relatively low.

Figure 6:
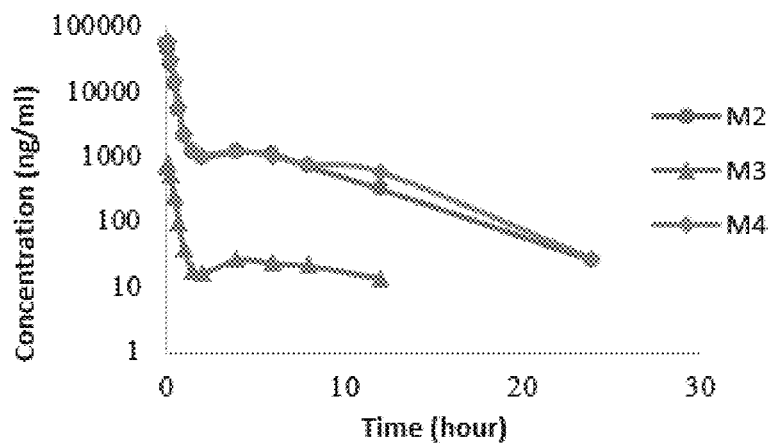
FIG. 6 shows the drug-time curve of each metabolite in rat plasma after intravenous injection of $I_{1s}$.

2. After intravenous injection, the blood concentration first declined rapidly with time, which might be related to rapid distribution of the drug in the body. Subsequently, the blood concentration dropped relatively slowly and entered an elimination phase. In combination with the semi-logarithmic-time curve of blood concentration, the drug basically conforms to the characteristics of a two-compartment model (see FIG. 6).

3. According to the pharmacokinetic parameters, the half-lives ($t_{1/2}$) of the main active metabolites M2 and M4 in plasma were both about 3 h (see Table 9), and were longer than the half-lives of NBP (44 min) and PHPB (45 min) (*Acta Pharmacol Sin.*, 2018, 39, 275-285).

4. According to the pharmacokinetic parameters, the apparent volumes of distribution Vz and clearance rates CL of M2, M3, and M4 were relatively large, suggesting that they were widely distributed in the body and could be quickly distributed from plasma to peripheral tissue or brain tissue (See Table 9).

TABLE 9

Pharmacokinetic parameters of each metabolite in rats after administration of $I_{1s}$

| Parameter | Unit | M2 | | | M3 | | | M4 | | |
|---|---|---|---|---|---|---|---|---|---|---|
| | | 1 | 2 | 3 | 1 | 2 | 3 | 1 | 2 | 3 |
| $t_{1/2}$ | h | 2.71 | 3.34 | 3.87 | 5.13 | 5.79 | 16.57 | 2.99 | 3.43 | 3.39 |
| Cmax | ng/ml | 51434.8 | 53513.2 | 52069.2 | 736.7 | 876.5 | 569.2 | 69795.2 | 65700.2 | 52513.6 |
| AUC(0-t) | h*ng/ml | 31712.4 | 28614.9 | 28503.7 | 517.6 | 577.8 | 492.6 | 40061.1 | 34160.8 | 32828.9 |
| AUC(0-∞) | h*ng/ml | 31765.4 | 28748.5 | 28703.5 | 624.1 | 673.9 | 858.7 | 40153.8 | 34287.8 | 32988.3 |
| Vz | ml/kg | 3075.2 | 4184.2 | 4858.4 | 296272.1 | 310110.9 | 695865.2 | 2683.8 | 3610.5 | 3704.0 |
| Cl | ml/h/kg | 787.02 | 869.61 | 870.97 | 40054.77 | 37097.53 | 29113.43 | 622.61 | 729.12 | 757.84 |

Figure 7:
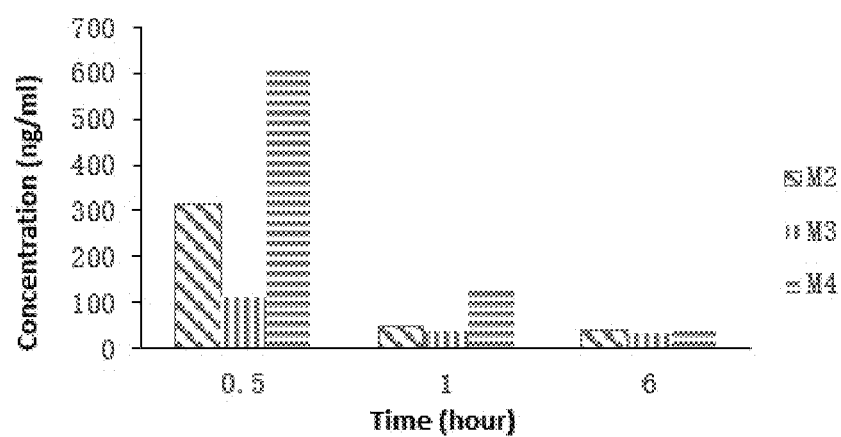
FIG. 7 shows the drug-time curve, drug concentration histogram, of each metabolite in rat brain tissue after intravenous injection of $I_{1s}$.

5. The active metabolites M2, M3, and M4 could all be detected in brain tissue. The concentration of M4 in the brain is higher than those of equimolar doses of NBP and PHPB (*Acta Pharmacol Sin.*, 2018, 39, 275-285), and the M2, M3, and M4 were quickly eliminated over time, indicating that the M2, M3, and M4 could all pass through the blood-brain barrier, were beneficial to play a role in the brain tissue, and would not accumulate in the brain for a long time to cause toxicity (see Table 10 and FIG. 7).

TABLE 10

Concentration data of each metabolite in rat brain tissue after intravenous injection of $I_{1s}$

| | Concentration in brain tissue (ng/g) | | | | | | | | | | | |
|---|---|---|---|---|---|---|---|---|---|---|---|---|
| Time | M2 | | | | M3 | | | | M4 | | | |
| (h) | 1 | 2 | 3 | Mean | 1 | 2 | 3 | Mean | 1 | 2 | 3 | Mean |
| 0.5 | 326.26 | 296.36 | 322.22 | 314.95 | 76.81 | 118.09 | 137.01 | 110.64 | 633.25 | 556.35 | 627.76 | 605.79 |
| 1 | 375.34* | 39.11 | 58.82 | 48.96 | 35.51 | 39.47 | 32.78 | 35.92 | 388.42* | 131.66 | 119.84 | 125.75 |
| 6 | 26.11 | 46.98 | 46.66 | 39.92 | 31.14 | 31.33 | 32.14 | 31.54 | 51.78 | 27.06 | 30.85 | 36.56 |

Conclusion: The compound L-arginine (S)-2-(1-acetoxy-n-pentyl) benzoate ($I_{1s}$) has excellent pharmacokinetic properties.

Example 19: Inhibitory Activity on Cyclooxygenase (COX)

Test Instruments:

SB-5200DT ultrasonic cleaner, Ningbo Scientz Biotechnology Co., Ltd.; YC-300L medicine storage cabinet, Zhongke Meiling Cryogenics Co., Ltd.; GZX-9140MBE blast drying oven, Shanghai Boxun Industrial Co., Ltd., Medical Equipment Factory; Direct-Q with pump ultrapure water meter, Millopore Corporation; BS224 electronic balance: Beijing Sartorius Instrument & System Co., Ltd.; 78-1 magnetic stirrer, Changzhou Guohua Electric Co., Ltd.; 3K15 low-temperature high-speed centrifuge, Sigma Corporation; Berthold LB941 microwell plate multifunctional microplate reader, Berthold Corporation.

Test Method:

The inhibition percentage of each sample on COX-1 and COX-2 was determined. The calculation formula is as follows: Inhibition rate (%)=(RFU100% enzyme activity control−RFU sample)/(RFU100% enzyme activity control−RFU blank control)×100%, wherein RFU is the relative fluorescence unit. For an inhibitor found to be effective, the $IC_{50}$ value was determined after testing the dose effect of the inhibitor.

Test Result:

TABLE 11

IC$_{50}$ values of compounds inhibiting
the activity of COX-1 and COX-2

| | IC$_{50}$ (μM) | |
|---|---|---|
| Compd. | COX-1 | COX-2 |
| Aspirin | 24.27 ± 2.15 | 1132 ± 76.51 |
| I$_{1s}$ | 56.41 ± 3.79 | 1279 ± 102.5 |

Conclusion: The activity of the compound I$_{1s}$ in inhibiting COX-1 is significantly lower than that of aspirin, suggesting that the compound I$_{1s}$ has less adverse reactions of the gastrointestinal tract than aspirin. The activity of the compound I$_{1s}$ in inhibiting COX-2 is close to that of aspirin, suggesting that both the compound I$_{1s}$ and aspirin have considerable inhibitory effects on COX-2 mediated inflammation.

Example 20: Preliminary Safety Test

1. Acute Toxicity Test

Test Animals:

ICR mice, provided by Shanghai Lingchang Biotech Co., Ltd. The laboratory animal production license is SCXK (Shanghai) 2013-0018, the certificate number is 2013001834483, and the laboratory animal use license is SYXK (Jiangsu) 2017-0015. The mice are aged 5-6 weeks, weighing 18-22 g, female; and the number of animals is 50.

Test Method:

On the basis of the preliminary experiment, the concentration gradient in the acute toxicity test of I$_{1s}$ was set to: 1500, 1300, 1100, 900, 700 mg/kg; and the corresponding drug concentration was: 150, 130, 110, 90, 70 mg/mL. The test drug was prepared into drug solutions of corresponding concentration for isometric administration (tail vein injection) once, various symptoms of poisoning and death in mice were recorded, and the dead animals were subjected to autopsy. The observation period is 14 days.

Test Result:

After the mice were injected with a higher dose of I$_{1s}$ in the tail vein, the mice had convulsions and decreased activity, and some mice died after 24 h. The dead mice in each group were dissected, and there was congestion in the precordial area, and no obvious abnormalities in the other organs. The body weight changes of each sample group are shown in Table 12, and the death distribution and LD$_{50}$ value (Bliss method) calculation results are shown in Table 13.

TABLE 12

The effect of intravenous injection of
compound I$_{1s}$ on body weight (M ± SD)

| | Dose | Body weight (g) | | |
|---|---|---|---|---|
| Group | (mg/kg) | D 1 | D 7 | D 14 |
| i.v. | 1500 | 19.9 ± 0.2 | 21.0 | 23.6 |
| | 1300 | 19.5 ± 0.4 | 20.8 ± 0.6 | 22.1 ± 0.6 |
| | 1100 | 19.4 ± 0.6 | 21.0 ± 0.5 | 22.0 ± 0.5 |
| | 900 | 19.8 ± 0.5 | 20.9 ± 0.6 | 22.2 ± 0.6 |
| | 700 | 19.4 ± 0.6 | 21.0 ± 0.6 | 22.3 ± 0.7 |

TABLE 13

Death and LD$_{50}$ value of intravenous injection of compound I$_{1s}$

| Group | Dose (mg/kg) | Number of animals (quantity) | Number of deaths (quantity) | LD$_{50}$ value (mg/kg) |
|---|---|---|---|---|
| i.v. | 1500 | 10 | 9 | 1119.5038 |
| | 1300 | 10 | 6 | (974.9831~1285.4466) |
| | 1100 | 10 | 4 | |
| | 900 | 10 | 2 | |
| | 700 | 10 | 1 | |

Conclusion: The LD$_{50}$ value of intravenous administration of the compound L-arginine (S)-2-(1-acetoxy-n-pentyl) benzoate (I$_{1s}$) is 1119.5038 mg/kg.

2. Test of Effect on hERG Potassium Channel

Using automatic patch clamp detection technology, the effects of the compound I$_{1s}$ and (S)—NBP on the hERG potassium channel of CHO-hERG cells at different administration concentrations were investigated. The results show that the IC$_{50}$ of I$_{1s}$ and (S)—NBP are both greater than 40 μM, but the inhibition rate (37.56%) of I$_{1s}$ at the maximum concentration is lower than that of (S)—NBP (41.45%), suggesting that the toxicity of the I$_{1s}$ to the heart may be lower than that of the (S)—NBP.

3. Bacterial Reverse Mutation Test

Microbial reverse mutation test (Ames test) was performed on the compound I$_{1s}$ to determine whether I$_{1s}$ has potential mutagenicity. The test bacteria are the histidine-deficient TA97, TA98, TA100 and TA102 strains of *Salmonella typhimurium*, and the dose range of the test sample is 0.1-1000 μg/dish. The test was performed under parallel conditions with and without a mixture of mammalian hepatomicrosome enzyme (S9), and the results were all negative.

Example 21: Preparation Method of Pharmaceutical Composition

1. Tablets

| Ingredients | Amount (mg/tablet) |
|---|---|
| (S)-2-(1-acyloxy-n-pentyl)benzoate | 50 |
| Starch | 30 |
| Microcrystalline cellulose | 20 |
| Magnesium stearate | 1 |
| Sodium carboxymethyl cellulose | 3 |

Preparation method: Active ingredients, starch, microcrystalline cellulose and sodium carboxymethyl cellulose were mixed uniformly according to proportions. The mixture was moistened with water and made into granules. The granules were dried and sized. Magnesium stearate was added, and after mixing, the mixture was pressed to obtain tablets of the product.

2. Capsules

| Ingredients | Amount (mg/capsule) |
|---|---|
| (S)-2-(1-acyloxy-n-pentyl)benzoate | 50 |
| Starch | 30 |
| Methylcellulose | 5 |
| Cross-linked PVP | 0.5 |

Preparation method: According to a formula, active ingredients and auxiliary agents were mixed, granulated and sieved, and the obtained mixture was fed into gastric-soluble hard capsules according to the quantitative amount to obtain capsules of the product.

3. Intravenous Injection

| Ingredients | Amount |
| --- | --- |
| (S)-2-(1-acyloxy-n-pentyl)benzoate | 10 mg/bottle |
| Water for injection | Appropriate amount |
| Sodium chloride for injection | Appropriate amount |

Preparation method: Water-soluble (S)-2-(1-acyloxy-n-pentyl)benzoate was dissolved in an appropriate amount of water for injection. An appropriate amount of sodium chloride for injection was added. Bottling and sterilization were performed under aseptic conditions to obtain intravenous injection fluid of the product.

4. Lyophilized Intravenous Injection

| Ingredients | Amount |
| --- | --- |
| (S)-2-(1-acyloxy-n-pentyl)benzoate | 10 mg/bottle |
| Water for injection | Appropriate amount |
| Mannitol | Appropriate amount |

Preparation method: Water-soluble (S)-2-(1-acyloxy-n-pentyl)benzoate was dissolved in an appropriate amount of water for injection and mannitol. After filtration, bottling and lyophilization, a lyophilized intravenous injection was obtained. When in use, the lyophilized intravenous injection is diluted with 0.9% normal saline or 5% dextrose injection for intravenous injection or intravenous drip.

What is claimed is:

1. A compound of General Formula I,

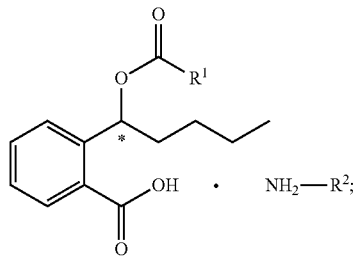

wherein:

$R^1$ is $C_1$-$C_8$ alkyl, aryl or heteroaryl; and $H_2N$—$R^2$ is basic amino acid or aminoguanidine.

2. The compound of General Formula I according to claim 1, wherein the chiral center of the 2-(1-acyloxy-n-pentyl) benzoic acid moiety represented by * is of an (R)-, (S)- or (R/S)-configuration.

3. The compound of General Formula I according to claim 1, wherein $R^1$ is methyl, ethyl, n-propyl or phenyl.

4. The compound of General Formula I according to claim 1, wherein the basic amino acid is L-arginine, L-lysine or L-histidine.

5. The compound of General Formula I according to claim 1, selected from the following compounds:

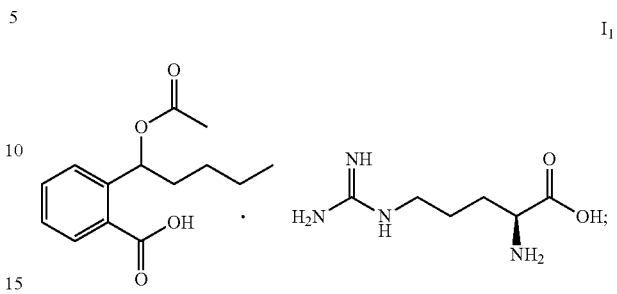

L-arginine (R/S)-2-(1-acetoxy-n-pentyl) benzoate

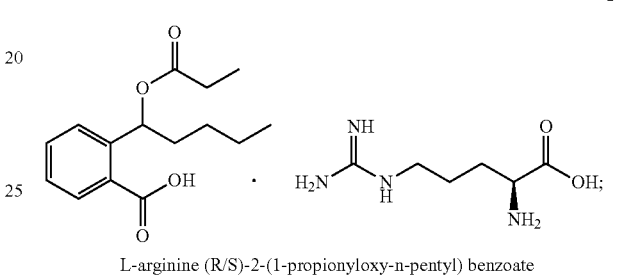

L-arginine (R/S)-2-(1-propionyloxy-n-pentyl) benzoate

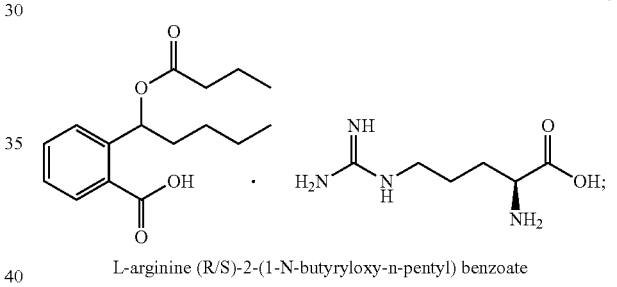

L-arginine (R/S)-2-(1-N-butyryloxy-n-pentyl) benzoate

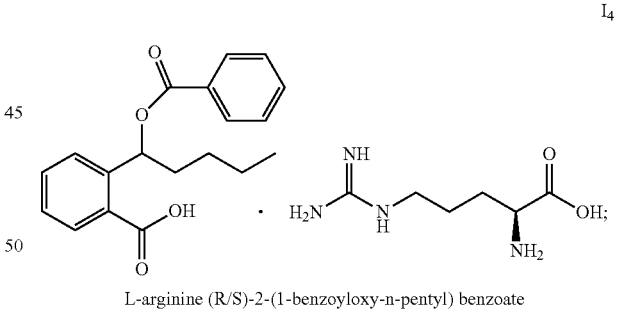

L-arginine (R/S)-2-(1-benzoyloxy-n-pentyl) benzoate

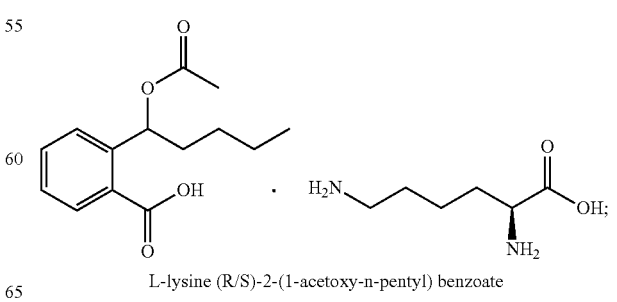

L-lysine (R/S)-2-(1-acetoxy-n-pentyl) benzoate

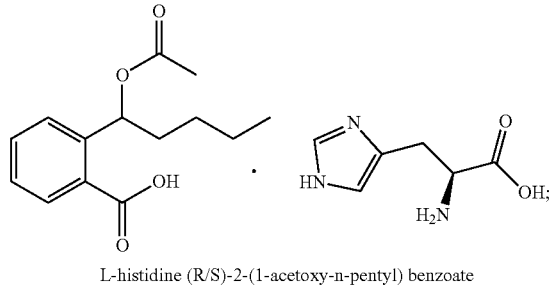

L-histidine (R/S)-2-(1-acetoxy-n-pentyl) benzoate

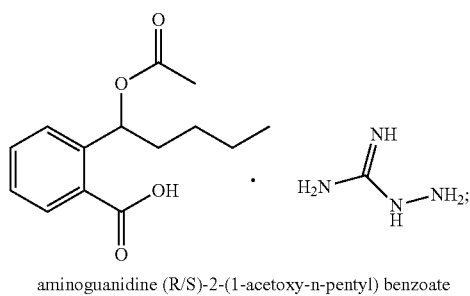

aminoguanidine (R/S)-2-(1-acetoxy-n-pentyl) benzoate

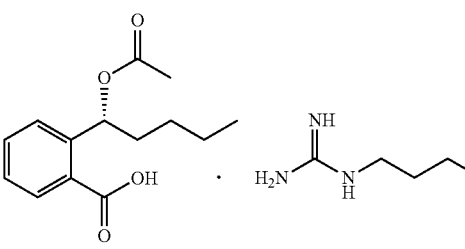

L-arginine (R)-2-(1-acetoxy-n-pentyl) benzoate

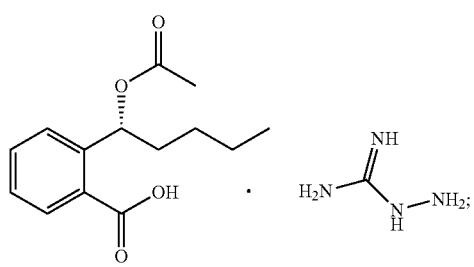

aminoguanidine (R)-2-(1-acetoxy-n-pentyl) benzoate

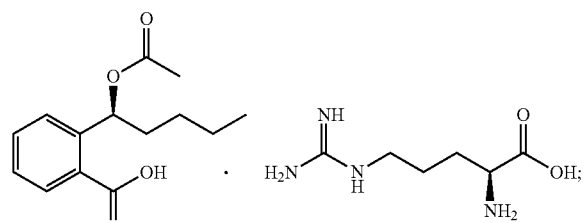

L-arginine (S)-2-(1-acetoxy-n-pentyl) benzoate

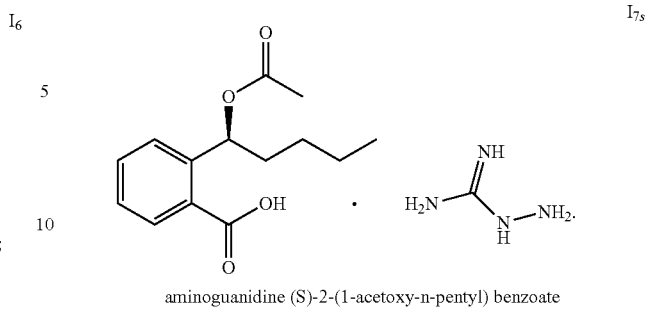

aminoguanidine (S)-2-(1-acetoxy-n-pentyl) benzoate

6. The compound of General Formula I according to claim 1, wherein the compound is prepared by the following steps:

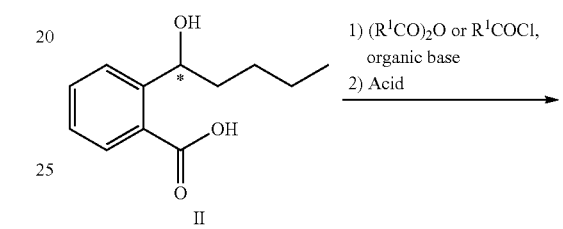

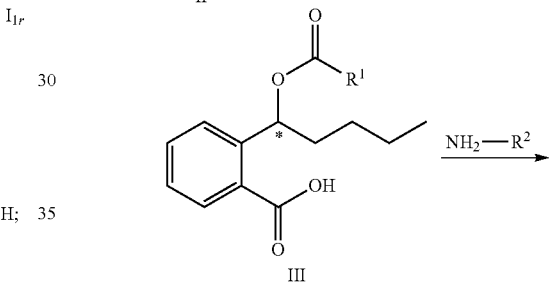

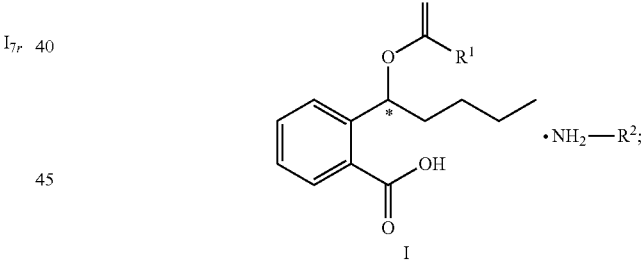

(1) at low temperature and in the presence of an organic base, adding acid anhydride or acyl chloride dropwise to an organic solvent solution of a compound II, and acidifying the reaction solution after the reaction for precipitating a white solid compound III; and (2) dissolving the compound III obtained in step (1) in alcohol, adding $H_2N-R^2$ to form a salt, and after the reaction, filtering and recrystallizing the precipitate with alcohol to obtain a compound I.

7. The compound of General Formula I according to claim 6, wherein in step (1), the reaction temperature is −30 to −5° C.; the organic base is 4-dimethylaminopyridine, diethylamine, triethylamine or pyridine; the organic solvent is one or a combination of two of diethyl ether, tetrahydrofuran, dichloromethane, trichloromethane or acetone; the acid is concentrated or dilute hydrochloric acid, sulfuric acid or nitric acid; and the reaction solution is acidified to pH 2-6.

8. The compound of General Formula I according to claim 6, wherein in step (2), the reaction temperature is −5 to 30° C., and the alcohol is ethanol, methanol, propanol or isopropanol.

9. A pharmaceutical composition, comprising the compound I according to claim 1 and a pharmaceutically acceptable carrier.

10. A method for preventing or treating ischemic cardiovascular and cerebrovascular diseases, resisting thrombosis and improving cardio-cerebral circulation disorders comprising a step of administrating a subject in need with the compound I according to claim 1.

* * * * *